(12) United States Patent
Weston

(10) Patent No.: US 11,058,807 B2
(45) Date of Patent: Jul. 13, 2021

(54) NEGATIVE PRESSURE DRESSING AND METHOD OF USING SAME

(71) Applicant: Smith & Nephew, Inc., Memphis, TN (US)

(72) Inventor: Richard Scott Weston, Carlsbad, CA (US)

(73) Assignee: Smith & Nephew, Inc., Memphis, TN (US)

( * ) Notice: Subject to any disclaimer, the term of this patent is extended or adjusted under 35 U.S.C. 154(b) by 964 days.

(21) Appl. No.: 15/441,899

(22) Filed: Feb. 24, 2017

(65) Prior Publication Data

US 2017/0258972 A1 Sep. 14, 2017

Related U.S. Application Data

(63) Continuation of application No. 14/610,806, filed on Jan. 30, 2015, now Pat. No. 9,610,390, which is a
(Continued)

(51) Int. Cl.
*A61M 1/00* (2006.01)
*A61F 13/02* (2006.01)
*A61F 13/00* (2006.01)

(52) U.S. Cl.
CPC ....... *A61M 1/0088* (2013.01); *A61F 13/0216* (2013.01); *A61F 2013/00174* (2013.01);
(Continued)

(58) Field of Classification Search
None
See application file for complete search history.

(56) References Cited

U.S. PATENT DOCUMENTS

| 1,480,562 A | 1/1924 | Mock |
| 2,195,771 A | 4/1940 | Estler |

(Continued)

FOREIGN PATENT DOCUMENTS

| DE | 561757 C | 10/1932 |
| DE | 1963258 | 6/1971 |

(Continued)

OTHER PUBLICATIONS

International Partial Search Report, International Application No. PCT/US2009/036829 dated Sep. 11, 2009, in 6 pages.
(Continued)

*Primary Examiner* — Kim M Lewis
(74) *Attorney, Agent, or Firm* — Knobbe, Martens, Olson & Bear, LLP

(57) ABSTRACT

The present invention relates to apparatuses and methods for treating a wound by applying reduced or negative pressure to the wound. The apparatus can include a wound cover, a fluid collection container, a vacuum pump, an inflation pump, and one or more conduits. The wound cover can be configured to move between at least a relatively rigid, generally raised position and a relatively flexible, generally collapsed position according to a predetermined program or in response to input from a user or one or more sensors. In some embodiments, the wound cover can be configured to move between at least the relatively rigid, generally raised position and the relatively flexible, generally collapsed position by adjusting the air pressure in one or more channels in the wound cover or by adjusting the length of piezoelectric or other length changing material supported by the wound cover.

21 Claims, 11 Drawing Sheets

Related U.S. Application Data continuation of application No. 12/922,130, filed as application No. PCT/US2009/036829 on Mar. 11, 2009, now Pat. No. 8,945,030.

(60) Provisional application No. 61/036,020, filed on Mar. 12, 2008.

(52) U.S. Cl.
CPC ....... *A61M 1/0025* (2014.02); *A61M 2205/18* (2013.01); *A61M 2205/3379* (2013.01)

(56) References Cited

U.S. PATENT DOCUMENTS

| | | |
|---|---|---|
| 3,171,410 A | 3/1965 | Towle, Jr. |
| 3,568,675 A | 3/1971 | Harvey |
| 3,633,567 A | 1/1972 | Sarnoff |
| 3,874,387 A | 4/1975 | Barbieri |
| 3,993,080 A | 11/1976 | Loseff |
| 4,112,947 A | 9/1978 | Nehring |
| 4,136,696 A | 1/1979 | Nehring et al. |
| 4,184,510 A | 1/1980 | Murry et al. |
| 4,224,945 A | 9/1980 | Cohen |
| 4,316,466 A | 2/1982 | Babb |
| 4,382,441 A | 5/1983 | Svedman |
| 4,465,485 A | 8/1984 | Kashmer et al. |
| 4,569,674 A * | 2/1986 | Phillips ............... A61M 27/00 604/119 |
| 4,573,965 A | 3/1986 | Russo |
| 4,608,041 A | 8/1986 | Nielsen |
| 4,691,695 A | 9/1987 | Birk et al. |
| 4,710,165 A | 12/1987 | McNeil et al. |
| 4,740,202 A | 4/1988 | Stacey et al. |
| 4,772,259 A | 9/1988 | Frech et al. |
| 4,778,446 A | 10/1988 | Jensen |
| 4,790,833 A | 12/1988 | Schmidt |
| 4,792,328 A | 12/1988 | Beck et al. |
| 4,921,488 A | 5/1990 | Maitz et al. |
| 4,969,880 A | 11/1990 | Zamierowski |
| 5,000,164 A | 3/1991 | Cooper |
| 5,055,198 A | 10/1991 | Shettigar |
| 5,073,172 A | 12/1991 | Fell |
| 5,100,396 A | 3/1992 | Zamierowski |
| 5,176,663 A | 1/1993 | Svedman et al. |
| 5,184,077 A | 2/1993 | Day et al. |
| 5,234,462 A | 8/1993 | Paveltic |
| 5,261,893 A | 11/1993 | Zamierowski |
| 5,328,614 A | 7/1994 | Matsumura |
| 5,358,494 A | 10/1994 | Svedman |
| 5,380,280 A | 1/1995 | Peterson |
| 5,419,768 A | 5/1995 | Kayser |
| 5,429,601 A | 7/1995 | Conley et al. |
| 5,449,347 A | 9/1995 | Preen et al. |
| 5,450,858 A | 9/1995 | Zablotsky et al. |
| 5,498,338 A | 3/1996 | Kruger et al. |
| 5,548,562 A | 8/1996 | Helgerud et al. |
| 5,549,584 A | 8/1996 | Gross |
| 5,618,556 A | 4/1997 | Johns et al. |
| 5,635,201 A | 6/1997 | Fabo |
| 5,636,643 A | 6/1997 | Argenta |
| 5,645,081 A | 7/1997 | Argenta |
| 5,759,570 A | 6/1998 | Arnold |
| 5,843,025 A | 12/1998 | Shaarit |
| 6,058,331 A * | 5/2000 | King ................. A61N 1/3605 607/2 |
| 6,135,116 A | 10/2000 | Vogel et al. |
| 6,142,982 A | 11/2000 | Hunt |
| 6,159,160 A | 12/2000 | Hsei et al. |
| 6,200,596 B1 | 3/2001 | Schwartzmiller et al. |
| 6,254,567 B1 | 7/2001 | Treu et al. |
| 6,398,767 B1 | 6/2002 | Fleischmann |
| 6,458,109 B1 | 10/2002 | Henley et al. |
| 6,465,708 B1 | 10/2002 | Augustine |
| 6,471,685 B1 | 10/2002 | Johnson |
| 6,547,756 B1 | 4/2003 | Greter et al. |
| 6,626,827 B1 | 9/2003 | Felix et al. |
| 6,676,610 B2 | 1/2004 | Morton et al. |
| 6,685,681 B2 | 2/2004 | Lockwood et al. |
| 6,695,824 B2 | 2/2004 | Howard et al. |
| 6,752,794 B2 | 6/2004 | Lockwood et al. |
| 6,755,807 B2 | 6/2004 | Risk, Jr. et al. |
| 6,794,554 B2 | 9/2004 | Sessions et al. |
| 6,856,821 B2 | 2/2005 | Johnson |
| 6,904,631 B2 | 6/2005 | Vrzalik et al. |
| 6,979,324 B2 | 12/2005 | Bybordi et al. |
| 6,994,702 B1 | 2/2006 | Johnson |
| 7,004,915 B2 | 2/2006 | Boynton et al. |
| 7,022,113 B2 | 4/2006 | Lockwood et al. |
| 7,108,683 B2 | 9/2006 | Zamierowski |
| 7,128,735 B2 | 10/2006 | Weston |
| 7,195,624 B2 | 3/2007 | Lockwood |
| 7,214,202 B1 | 5/2007 | Vogel et al. |
| 7,216,651 B2 | 5/2007 | Argenta et al. |
| 7,361,184 B2 | 4/2008 | Joshi |
| 7,494,482 B2 | 2/2009 | Orgill et al. |
| 7,524,315 B2 | 4/2009 | Blott et al. |
| 7,534,927 B2 | 5/2009 | Lockwood et al. |
| 7,611,500 B1 | 11/2009 | Lina et al. |
| 7,615,036 B2 | 11/2009 | Joshi et al. |
| 7,651,484 B2 | 1/2010 | Heaton et al. |
| 7,699,830 B2 | 4/2010 | Martin |
| 7,708,724 B2 | 5/2010 | Weston |
| 7,753,894 B2 | 7/2010 | Blott et al. |
| 7,776,028 B2 | 8/2010 | Miller et al. |
| 7,779,625 B2 | 8/2010 | Joshi et al. |
| 7,790,945 B1 | 9/2010 | Watson, Jr. |
| 7,794,450 B2 | 9/2010 | Blott et al. |
| 7,846,141 B2 | 12/2010 | Weston |
| 7,883,494 B2 | 2/2011 | Martin |
| 7,896,856 B2 | 3/2011 | Petrosenko et al. |
| 7,909,805 B2 | 3/2011 | Weston |
| 7,947,033 B2 | 5/2011 | Ganapathy et al. |
| 7,964,766 B2 | 6/2011 | Blott et al. |
| 7,998,125 B2 | 8/2011 | Weston |
| 8,007,257 B2 | 8/2011 | Heaton et al. |
| 8,062,272 B2 | 11/2011 | Weston |
| 8,062,273 B2 | 11/2011 | Weston |
| 8,100,887 B2 | 1/2012 | Weston |
| 8,105,295 B2 | 1/2012 | Blott et al. |
| 8,118,794 B2 | 2/2012 | Weston |
| 8,162,909 B2 | 4/2012 | Blott et al. |
| 8,197,467 B2 | 6/2012 | Heaton et al. |
| 8,212,100 B2 * | 7/2012 | Moore ................ A61F 13/0216 602/43 |
| 8,235,955 B2 | 8/2012 | Blott et al. |
| 8,235,972 B2 | 8/2012 | Adahan |
| 8,257,327 B2 | 9/2012 | Blott et al. |
| 8,282,611 B2 | 10/2012 | Weston |
| 8,303,552 B2 | 11/2012 | Weston |
| 8,308,714 B2 | 11/2012 | Weston et al. |
| 8,323,264 B2 | 12/2012 | Weston et al. |
| 8,338,402 B2 | 12/2012 | Fry et al. |
| 8,348,910 B2 | 1/2013 | Blott et al. |
| 8,366,692 B2 | 2/2013 | Weston et al. |
| 8,449,509 B2 | 5/2013 | Weston |
| 8,480,641 B2 | 7/2013 | Jacobs |
| 8,540,699 B2 | 9/2013 | Miller et al. |
| 8,641,691 B2 | 2/2014 | Fink et al. |
| 8,708,998 B2 | 4/2014 | Weston et al. |
| 8,784,393 B2 | 7/2014 | Weston et al. |
| 8,795,243 B2 | 8/2014 | Weston |
| 8,852,149 B2 | 10/2014 | Weston et al. |
| 8,920,395 B2 | 12/2014 | Kazala, Jr. et al. |
| 8,945,030 B2 | 2/2015 | Weston |
| 8,974,429 B2 | 3/2015 | Gordon et al. |
| 9,044,579 B2 | 6/2015 | Blott et al. |
| 9,452,244 B2 | 9/2016 | Blott et al. |
| 9,610,390 B2 | 4/2017 | Weston |
| 9,999,711 B2 * | 6/2018 | Weston ............... A61M 1/0037 |
| 2002/0082544 A1 | 6/2002 | Thrash et al. |
| 2002/0115952 A1 | 8/2002 | Johnson |
| 2002/0161346 A1 | 10/2002 | Lockwood et al. |
| 2002/0183659 A1 | 12/2002 | Krause |

(56) References Cited

U.S. PATENT DOCUMENTS

| | | | |
|---|---|---|---|
| 2002/0198474 A1 | 12/2002 | Becker | |
| 2003/0021775 A1 | 1/2003 | Freeman | |
| 2003/0033032 A1 | 2/2003 | Lind et al. | |
| 2003/0144619 A1 | 7/2003 | Augustine | |
| 2003/0171675 A1 | 9/2003 | Rosenberg | |
| 2003/0212357 A1 | 11/2003 | Pace | |
| 2003/0216672 A1* | 11/2003 | Rastegar | A61H 9/0071 601/9 |
| 2004/0014131 A1 | 1/2004 | Benson et al. | |
| 2004/0064132 A1 | 4/2004 | Boehringer et al. | |
| 2004/0073151 A1* | 4/2004 | Weston | A61M 1/0027 602/41 |
| 2004/0122434 A1 | 6/2004 | Argenta et al. | |
| 2004/0127845 A1 | 7/2004 | Renz et al. | |
| 2004/0230132 A1 | 11/2004 | Shehada | |
| 2005/0065484 A1 | 3/2005 | Watson | |
| 2006/0079852 A1* | 4/2006 | Bubb | A61M 1/0027 604/317 |
| 2006/0173253 A1* | 8/2006 | Ganapathy | A61B 5/1468 600/310 |
| 2007/0014837 A1 | 1/2007 | Johnson et al. | |
| 2007/0021697 A1 | 1/2007 | Ginther et al. | |
| 2007/0038172 A1 | 2/2007 | Zamierowski | |
| 2007/0118096 A1 | 5/2007 | Smith et al. | |
| 2007/0129660 A1 | 6/2007 | McLeod et al. | |
| 2007/0185463 A1 | 8/2007 | Mulligan | |
| 2007/0219497 A1 | 9/2007 | Johnson et al. | |
| 2007/0219532 A1 | 9/2007 | Karpowicz et al. | |
| 2007/0299412 A1 | 12/2007 | Vogel | |
| 2008/0033324 A1 | 2/2008 | Cornet et al. | |
| 2008/0041401 A1 | 2/2008 | Casola et al. | |
| 2008/0132819 A1 | 6/2008 | Radl et al. | |
| 2008/0146892 A1 | 6/2008 | Leboeuf | |
| 2008/0167593 A1 | 7/2008 | Fleischmann | |
| 2008/0200906 A1 | 8/2008 | Sanders et al. | |
| 2008/0208147 A1 | 8/2008 | Argenta et al. | |
| 2008/0234641 A1 | 9/2008 | Locke et al. | |
| 2008/0294147 A1 | 11/2008 | Radl et al. | |
| 2008/0306456 A1 | 12/2008 | Riesinger | |
| 2009/0036873 A1 | 2/2009 | Nielsen et al. | |
| 2009/0043268 A1 | 2/2009 | Eddy et al. | |
| 2009/0054855 A1 | 2/2009 | Blott et al. | |
| 2009/0105671 A1 | 4/2009 | Daggar et al. | |
| 2009/0157016 A1 | 6/2009 | Adahan | |
| 2009/0221977 A1 | 9/2009 | Blott et al. | |
| 2009/0299308 A1 | 12/2009 | Kazala, Jr. et al. | |
| 2009/0299340 A1 | 12/2009 | Kazala, Jr. et al. | |
| 2009/0312723 A1 | 12/2009 | Blott et al. | |
| 2010/0022990 A1 | 1/2010 | Karpowicz et al. | |
| 2010/0036367 A1 | 2/2010 | Krohn | |
| 2010/0049151 A1 | 2/2010 | Aicher | |
| 2010/0057025 A1 | 3/2010 | Aicher | |
| 2010/0063483 A1 | 3/2010 | Adahan | |
| 2010/0211030 A1 | 8/2010 | Turner et al. | |
| 2010/0249733 A9 | 9/2010 | Blott et al. | |
| 2010/0268128 A1 | 10/2010 | Randolph | |
| 2011/0118683 A1 | 5/2011 | Weston | |
| 2011/0251569 A1 | 10/2011 | Turner et al. | |
| 2012/0001762 A1 | 1/2012 | Turner et al. | |

FOREIGN PATENT DOCUMENTS

| | | |
|---|---|---|
| DE | 4012232 A1 | 10/1991 |
| DE | 19844355 A1 | 4/2000 |
| EP | 0853950 B1 | 10/2002 |
| EP | 0880953 B1 | 10/2003 |
| FR | 1163907 A | 10/1958 |
| GB | 114754 A | 4/1918 |
| GB | 641061 A | 8/1950 |
| GB | 1224009 A | 3/1971 |
| GB | 1549756 A | 8/1979 |
| GB | 2195255 A | 4/1988 |
| GB | 2235877 A | 3/1991 |
| GB | 2378392 A | 2/2003 |
| JP | H09-503923 A | 4/1997 |
| SU | 1251912 A1 | 8/1986 |
| WO | WO 84/01904 A1 | 5/1984 |
| WO | WO 90/11795 A1 | 10/1990 |
| WO | WO 91/16030 A1 | 10/1991 |
| WO | WO 96/05873 A1 | 2/1996 |
| WO | WO 2000/21586 | 4/2000 |
| WO | WO 01/24709 A1 | 4/2001 |
| WO | WO 2003/070135 | 8/2003 |
| WO | WO 2006/014764 A2 | 2/2006 |
| WO | WO 2006/114637 | 11/2006 |
| WO | WO 2007/062024 | 5/2007 |
| WO | WO 2007/087809 | 8/2007 |
| WO | WO 2008/027449 | 3/2008 |
| WO | WO 2008/143628 | 11/2008 |
| WO | WO 2009/158131 | 12/2009 |
| WO | WO 2012/078723 | 6/2012 |

OTHER PUBLICATIONS

International Report on Patentability, re PCT Application No. PCT/US2009/036829, dated Sep. 14, 2010.

International Search Report and Written Opinion, re PCT Application No. PCT/US2009/036829, dated Nov. 27, 2009.

Bagautdinov, "Variant of External Vacuum Aspiration in the Treatment of Purulent Diseases of Soft Tissues," Current Problems in Modern Clinical Surgery, 1986, 4 pages.

Chariker, M.E., et al, "Effective Management of Incisional and Cutaneous Fistulae with Closed Suction Wound Drainage," Contemporary Surgery. Jun. 1989, pp. 59-63, vol. 34 USA.

Eaglstein, W.H., et al., Wound Dressings: Current and Future, *Clin. and Exper. Approaches to Dermal and Epidermal Repair: Normal and Chronic Wounds*, 1991, 257-265.

Eisenbud, D.E., Modern Wound Management, *Anadem Publishing*, Chap. 16, 109-116, 2000.

Froberg, Birgitta et al., Vacusac Therapy—A Supplement to the Treatment of Varicose Ulcers? (Stockholm) 1990, in 37 pages.

Jeter, Katherine F. et, Managing Draining Wounds and Fistulae: New and Established Methods, Chronic Wound Care, Chapter 27, pp. 240-246, 1990.

Landis, E.M. and J.H. Gibbon, Jr., The Effects of Alternate Suction and Pressure on Blood Flow to the Lower Extremities, Alternate Suction and Pressure, J Clin Invest. Sep. 1933, 12(5): 925-961.

Nursing75, Wound Suction: Better Drainage with Fewer Problems, Nursing, vol. 5, No. 10, Oct. 1975, pp. 52-55.

Westaby, S., et al., "A Wound Irrigation Device", The Lancet, Sep. 2, 1978, pp. 503-504.

Witkowski, J.A. and Parish, L.C., Synthetic Dressings: Wound Healing in the '80s, *Hospital Therapy*, Nov. 1986, 75-84.

Arnljots B., et al., "Irrigation Treatment in Split-Thickness Skin Grafting of Intractable Leg Ulcers," Scandinavian Journal of Plastic and Reconstructive Surgery, vol. 19, 1985, pp. 211-213.

Aubrey D.A. et al., "Treatment of the Perineal Wound after Proctectomy by Intermittent Irrigation," Arch. Surg, vol. 119, Oct. 1984, pp. 1141-1144.

Dilmaghani a., et al., "A Method for Closed Irrigation and Suction Therapy in Deep Wound Infections," Journal of Bone and Joint Surgery, Mar. 1969, vol. 51-A(2), pp. 323-342.

Fleck C.A., et al., "When Negative is Positive: A Review of Negative Pressure Wound therapy," Wound Care, Mar./Apr. 2004, pp. 20-25.

Gupta S., et al., "Guidelines for Managing Pressure Ulcers with Negative Pressure Wound Therapy," Advances in Skin & Wound Care, vol. 17, Supplement 2, Nov./Dec. 2004, pp. 1-16.

Hartz R.S., et al., "Healing of the Perineal Wound," The Archives of Surgery, Apr. 1980, vol. 115, pp. 471-474.

International Search Report and Written Opinion for Application No. PCT/US2009/030497, dated Sep. 28, 2009, 20 pages.

International Preliminary Report on Patentability for Application No. PCT/US2009/030497, dated Jul. 22, 2010, 14 pages.

Kloth L.C., et al., "Chapter 10—Adjunctive Interventions for Wound Healing," Wound Healing Alternatives in Management, 3rd Edition, 2002, pp. 339-352.

(56) References Cited

OTHER PUBLICATIONS

Mendez-Eastman S., "Guidelines for Using Negative Pressure Wound Therapy," Advances in Skin & Wound Care, The Journal for Prevention and Healing, vol. 14 (6), Nov./Dec. 2001, pp. 314-325.

Meyer W., et al., "In Surgery, Medicine and the Specialties a Manual of its Practical Application", Bier's Hyperemic Treatment, W.B. Saunders Company, 1908, pp. 44-65.

Morykwas M.J., et al., "Effects of Varying Levels of Subatmospheric Pressure on the Rate of Granulation Tissue Formation in Experimental Wounds in Swine," Annals of Plastic Surgery, Abstract, vol. 47, 2001, p. 547.

Morykwas M.J., et al., "Vacuum-Assisted Closure: A New Method for Wound Control and Treatment: Animal Studies and Basic Foundation," Annals Plastic Surgery, vol. 38 (6), Jun. 1997, pp. 553-562.

Solovev V. A, et al., "The Method of Treatment of Immature External Fistulas in the Upper Gastrointestinal Tract—Guidelines" USSR Ministry of Health, S. M. Kirov Gorky State Medical Institute, 1987, 11 pages.

Solovev V.A., "Treatment and Prevention of Suture Failures after Gastric Resection," Dissertation Abstract, Gorky, 1988, 51 pages.

Svedman P., "A Dressing Allowing Continuous Treatment of a Biosurface," IRCS Medical Science: Biomedical Technology; Clinical Medicine; Surgery and Transplantation, vol. 7, 1979, p. 221.

Svedman P., "Irrigation Treatment of Leg Ulcers," The Lancet, Sep. 3, 1983, pp. 532-534.

Svedman P., et al., "A Dressing System Providing Fluid Supply and Suction Drainage Used for Continuous or Intermittent Irrigation," Annals of Plastic Surgery, vol. 17 (2), Aug. 1986, 9 pages.

Swift S., et al., "Quorum Sensing in Aeromonas Hydrophila and Aeromonas Salmoncida: Identification of LuxRI Homologs AhyRI and AsaRI and Their Cognate N-Acylhomoserine Lactone Signal Molecules," Journal of Bacteriology, Sep. 1997, vol. 179, No. 17, pp. 5271-5281.

Teder H., et al., "Continuous Wound Irrigation in the Pig," Journal of Investigative Surgery, 1990, vol. 3, pp. 399-407.

Tittel K., et al., "New Standards in Postoperative Wound Drainage," Unfallchirurgie, vol. 14 (2), 1988, pp. 104-107.

Tribble D E., "An Improved Sump Drain-Irrigation Device of Simple Construction," Archives of Surgery, vol. 105, Sep. 1972, pp. 511-513.

Urschel J. D., et al., "The Effect of Mechanical Stress on Soft and Hard Tissue Repair; A Review," British Journal of Plastic Surgery, vol. 41, 1988, pp. 182-186.

Viljanto J., et al., "Local Hyperalimentation of Open Wounds," Br. J. Surg., vol. 63, 1976, pp. 427-430.

Wooding-Scott M., et al., "No Wound is Too Big for Resourceful Nurses," RN, Dec. 1988, pp. 22-25.

Zivadinovic G., et al., "Vacuum Therapy in the Treatment of Peripheral Blood Vessels," Timocki Medicinski Glasnik, Conference Papers of the 5th Timok Medical Days, Majdanpek, 1986, pp. 161-164.

* cited by examiner

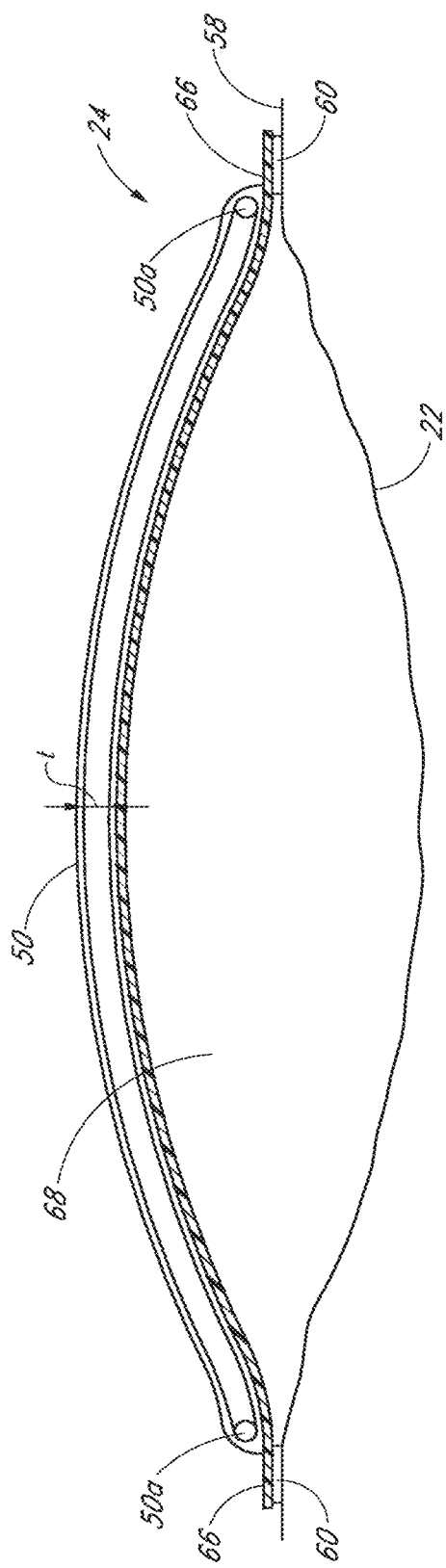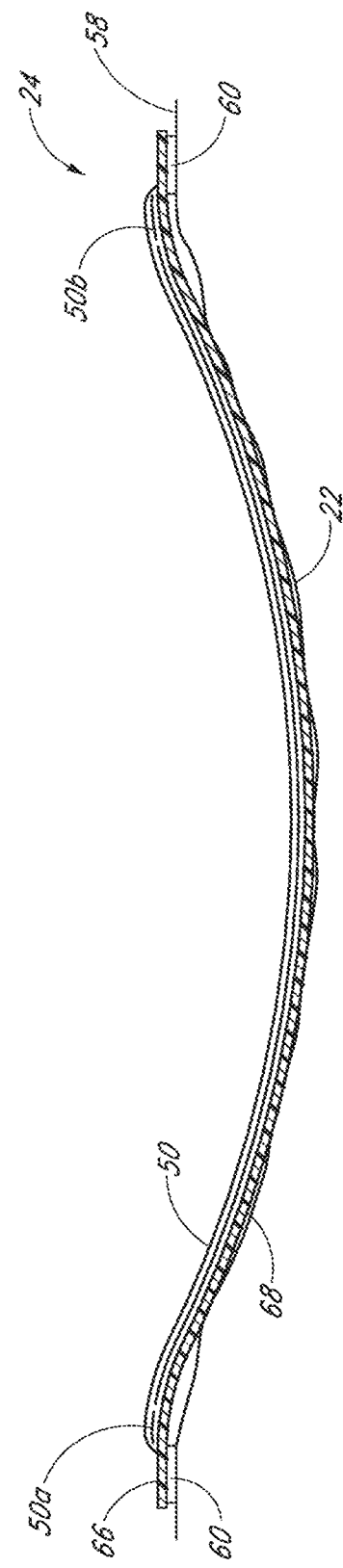
FIG. 3A
FIG. 3B

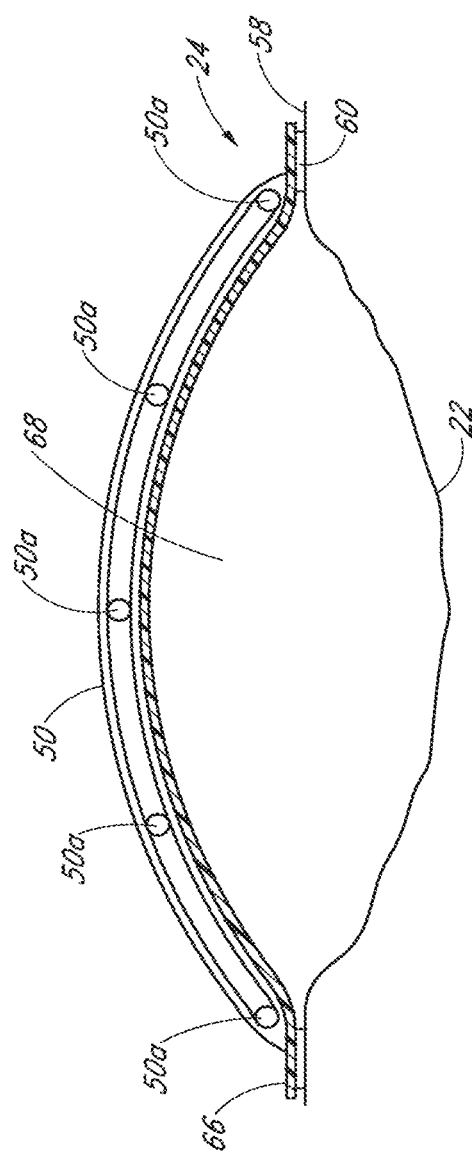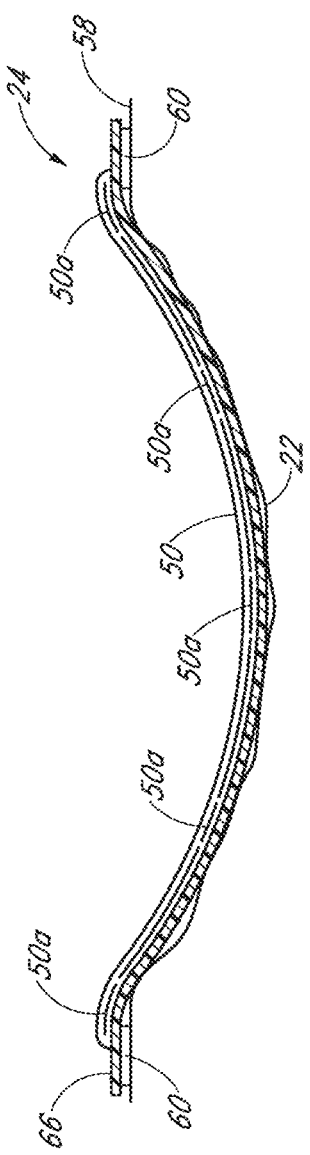
FIG. 4A
FIG. 4B

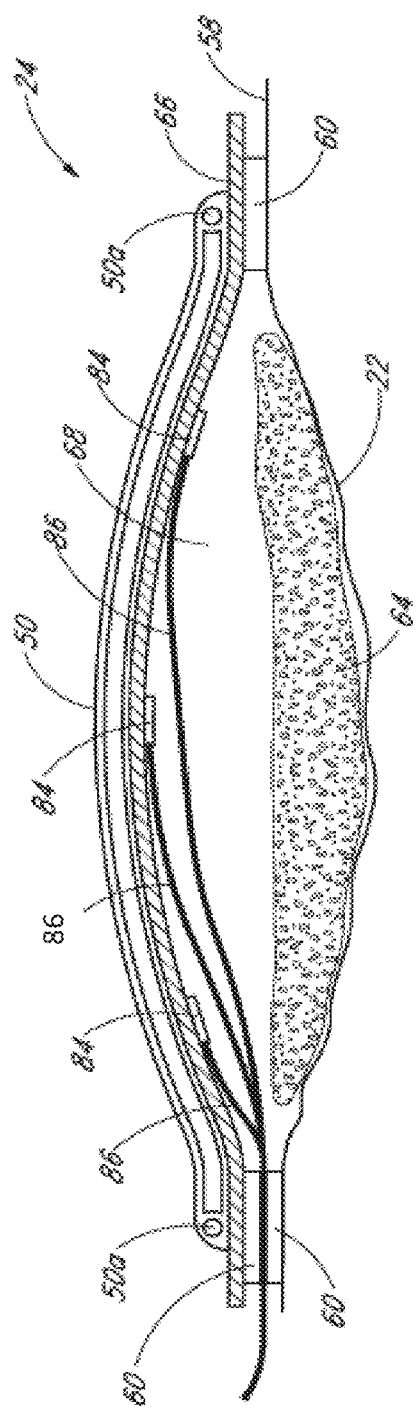

NEGATIVE PRESSURE DRESSING AND METHOD OF USING SAME

CROSS-REFERENCE TO RELATED APPLICATIONS

This application is related to, and claims the benefit of, U.S. Provisional Patent Application No. 61/036,020, filed Mar. 12, 2008, the entirety of which is hereby incorporated by reference herein and made a part of the present disclosure.

BACKGROUND OF THE INVENTION

Field of the Invention

Certain embodiments of the present application relate to treating a wound by applying reduced or negative pressure to the wound.

Description of the Related Art

The treatment of open or chronic wounds that are too large to spontaneously close or otherwise fail to heal has long been a troublesome area of the medical practice. Closure of an open wound requires inward migration of surrounding epithelial and subcutaneous tissue. Some wounds, however, are sufficiently large or infected that they are unable to heal spontaneously. In such instances, a zone of stasis in which localized edema restricts the flow of blood to the epithelial and subcutaneous tissue forms near the surface of the wound. Without sufficient blood flow, the wound is unable to successfully fight bacterial infection and is accordingly unable to close spontaneously.

An initial stage of wound healing is characterized by the formation of granulation tissue which is a matrix of collagen, fibronectin, and hyaluronic acid carrying macrophages, fibroblasts, and neovasculature that forms the basis for subsequent epithelialization of the wound. Infection and poor vascularization hinder the formation of granulation tissue within wounded tissue, thereby inhibiting wound healing. It therefore becomes desirable to provide a technique for increasing blood circulation within wounded tissue to promote spontaneous healing and to reduce infection.

Another problem encountered during the treatment of wounds is the selection of an appropriate technique for wound closure during the healing process. Sutures are often used to apply force to adjacent viable tissue in order to induce the edges of a wound to migrate together and heal. However, sutures apply a closure force to only a very small percentage of the area surrounding a wound. When there is scarring, edema, or insufficient tissue, the tension produced by the sutures can become great, causing excessive pressure to be exerted by the sutures upon the tissue adjacent to each suture. As a result, the adjacent tissue often becomes ischemic, thereby rendering suturing of large wounds counterproductive. If the quantity or size of the sutures is increased to reduce the tension required of any single suture, the quantity of foreign material within the wound is concomitantly increased and the wound is more apt to become infected. Additionally, the size or type of a particular wound can prevent the use of sutures to promote wound closure. It therefore becomes desirable to provide an apparatus and method for closing a large wound that distributes a closure force evenly about the periphery of the wound.

Wounds resulting from ischemia, or lack of blood flow, are also often difficult to heal since decreased blood flow to a wound can inhibit normal immune reaction to fight infection. Patients that are bedridden or otherwise non-ambulatory are susceptible to such ischemic wounds as decubitus ulcers or pressure sores. Decubitus ulcers form as a result of constant compression of the skin surface and underlying tissue thus restricting circulation. Since the patient is often unable to feel the wound or to move sufficiently to relieve the pressure, such wounds can become self-perpetuating. Although it is common to treat such wounds with flaps, the conditions that initially caused the wound can also work against successful flap attachment. Wheelchair-bound paraplegics, for example, must still remain seated after treatment of pelvic pressure sores. It therefore becomes desirable to provide a treatment procedure for ischemic wounds that can be conducted in situ upon an immobile or partially mobile patient.

Other types of wounds in which ischemia leads to progressive deterioration include partial thickness burns. A partial thickness burn is a burn in which the cell death due to thermal trauma does not extend below the deepest epidermal structures such as hair follicles, sweat glands, or sebaceous glands. The progression of partial thickness burns to deeper burns is a major problem in burn therapy. The ability to control or diminish the depth of burns greatly enhances the prognosis for burn patients and decreases morbidity resulting from burns. Partial thickness burns are formed of a zone of coagulation, which encompasses tissue killed by thermal injury, and a zone of stasis. The zone of stasis is a layer of tissue immediately beneath the zone of coagulation. Cells within the zone of stasis are viable, but the blood flow is static because of collapse of vascular structures due to localized edema. Unless blood flow is re-established within the zone of stasis soon after injury, the tissue within the zone of stasis also dies. The death of tissue within the zone of stasis is caused by lack of oxygen and nutrients, reperfusion injury (re-establishment of blood flow after prolonged ischemia), and decreased migration of white blood cells to the zone resulting in bacterial proliferation. Again, it becomes desirable to provide a technique for treating burn wounds by enhancing blood circulation to the wounded tissue to inhibit burn penetration.

Negative pressure wound therapy has been around for many years and has been proven to assist with the healing of wounds. There have been two distinctive types of negative pressure wound covers, one is flexible membrane technology which is very common in the United States, and the other type is a rigid dome arrangement that has been used in Russia since at least the mid 70's. Both have advantages and disadvantages in wound treatment therapy. For example, the flexible membrane configuration may be more advantageous for some types of wounds, during certain cycles of treatment, or even for certain portions of the body that have non-planar surface geometries. However, for certain wounds or during certain cycles of the wound therapy, there may be advantages to using rigid dome wound covers, such as increasing blood flow through the wound bed.

Additionally, as mentioned, there may be advantages to cycling between the semi-rigid configuration and the collapsed configuration for one particular wound that is being treated. It may therefore be desirable to have a wound cover that can change from a rigid configuration to a collapsed configuration easily and efficiently during the course of treatment. However, the existing apparatuses available in the field do not have this ability. Therefore, there is a need for a wound cover that can be changed from the semi-rigid configuration to the collapsed configuration during the course of treatment.

SUMMARY OF THE INVENTION

Certain embodiments disclosed herein are directed to systems, methods and apparatuses for wound therapy. However, it will be appreciated that the systems, methods and apparatuses may have application to other fields. In certain preferred embodiments, the wounds being treated may include, but are not limited to, acute and chronic wounds, orthopedic trauma wounds, and post-Cesarean wounds, to name a few.

In some embodiments, such wounds are treated using a negative pressure wound therapy apparatus that can comprise a wound cover, a fluid collection container, a vacuum pump comprising a pump motor, and tubing or conduit. In addition, in some embodiments, the apparatus can include a pressure sensor that measures a pressure in the conduit. In some embodiments, one or more tubes of the conduit can channel a fluid between the wound cover, the fluid collection container, and the pump. In addition, in some embodiments, first and second control circuits can be provided for controlling the pump motor without using a processor.

In some embodiments, such wounds are treated using a negative pressure wound therapy apparatus which can comprise a wound cover, a fluid collection container, a pump unit comprising one or more vacuum and/or inflation pump motors, and conduit. In some embodiments, such wounds are treated using an apparatus for covering a wound and facilitating the application of negative pressure wound therapy to the wound, comprising a wound cover sized and configured to be placed over and enclose the wound so as to define a space between the wound cover and the wound and to maintain a reduced pressure in the space when reduced pressure is applied to the space. In some embodiments, when the wound cover is placed over and encloses the wound and negative pressure is applied to the space, the wound cover can be configured to move between at least a relatively rigid, generally raised position and a relatively flexible, generally collapsed position wherein a volume of the space between the wound cover and the wound being generally greater in the generally raised position than in the generally collapsed position.

In some embodiments, such wounds are treated using a wound cover for covering a wound, wherein the wound cover can comprise a generally flexible, fluid impermeable or semi-permeable cover or member and at least one channel provided along at least a portion of the cover. In some embodiments, the wound cover can be configured to become relatively rigid during application of negative pressure to the space and when a positive pressure is supplied to the at least one channel, so as to increase the volume of the space between the cover and the wound. In some embodiments, the wound cover can be configured to become relatively flexible during application of negative pressure to the space and when the positive pressure is removed from the at least one channel, so as to collapse the wound cover in the approximate direction of the wound. In some embodiments, the member can be sized and configured to be placed over and enclose the wound so as to define a space between the member and the wound and to maintain a reduced pressure in the space when negative pressure is applied to the space.

In some embodiments, such wounds are treated using a wound cover configured to enclose the wound, wherein the wound cover can comprise at least one channel or pocket formed in the cover configured to provide an enclosed volume. In some embodiments, the at least one channel or pocket can comprise at least one port or opening configured to permit fluid to pass from a supply of fluid pressure into or out of the at least one channel or pocket.

In some embodiments, such wounds are treated using an apparatus for administering reduced pressure treatment to a wound on a body, the apparatus comprising a wound cover for covering a wound and facilitating the application of negative pressure wound therapy to the wound, a fluid collection container, a vacuum pump, and a control device. In some embodiments, the wound cover can comprise a generally flexible, fluid impermeable or semi-permeable cover sized and configured to be placed over and enclose the wound so as to create a space between the cover and the wound, and a seal configured to seal at least a portion of the member to a portion of tissue surrounding the wound such that a reduced pressure is generally maintained in the space between the cover and the wound when the cover is placed over the wound and the space is supplied with reduced pressure.

In some embodiments, the member can be configured such that at least a portion of the member can be selectively moved between at least a generally raised position and a generally collapsed position when the member is placed over the wound and the space is supplied with reduced pressure, and such that the volume of the space between the member and the wound is greater in the generally raised position than in the generally collapsed position. In some embodiments, the vacuum pump can be configured to provide reduced pressure to the space between the member and the wound, and can comprise a pump motor and one or more tubes configured to at least channel the reduced pressure from the vacuum pump to the space between the wound cover and the wound and to channel a flow of fluid between the wound and the fluid collection container. In some embodiments, the control device can be configured so as to control the level of reduced pressure applied to the space between the wound cover and the wound and to selectively moved at least a portion of the member between at least the generally raised position and the generally collapsed position when the member is placed over the wound and the space is supplied with reduced pressure.

In some embodiments, such wounds are treated using a method comprising the steps of: providing a generally flexible, fluid impermeable or semi-permeable cover sized and configured to be placed over and enclose the wound so as to create a volume of space between the cover and the wound, sealing at least a portion of the cover to a portion of the patient's skin surrounding the wound such that a desired level of reduced pressure can be generally maintained in the volume between the cover and the wound when the cover is placed over the wound, providing a fluid collection container, a vacuum pump, and one or more tubes configured to at least channel a flow of fluid between the cover, the fluid collection container, and the vacuum pump, controlling the vacuum pump to at least provide a predetermined level of reduced pressure to the volume of space between the cover and the wound, and moving the cover between a generally raised position and a generally collapsed position, the volume of the space between the cover and the wound being greater in the generally raised position than in the generally collapsed position.

In some embodiments, such wounds are treated using a method comprising the steps of: placing a wound cover over the wound to enclose the wound, the wound cover being moveable between a first configuration that is raised above the wound while the wound cover encloses the wound to define an interior volume between the wound and the wound cover, and a second configuration wherein the wound cover encloses the wound and is collapsed toward the wound, and applying negative pressure to the wound while enclosed by the wound cover. In some embodiments, during application of negative pressure to the wound, the wound cover can remain raised above the wound when in its first configuration, and can collapse toward the wound when is in its second configuration.

BRIEF DESCRIPTION OF THE DRAWINGS

These and other features, aspects and advantages will now be described in connection with certain embodiments, in reference to the accompanying drawings. The illustrated embodiments, however, are merely examples and are not intended to be limiting. The following are brief descriptions of the drawings.

FIG. 3a is a section view of the wound cover of FIG. 1, taken through line 3a-3a in FIG. 2, illustrating the wound cover in the raised or rigid configuration.

FIG. 3b is a section view of the wound cover of FIG. 1, taken through line 3b-3b in FIG. 2, illustrating the wound cover in the deflated or collapsed configuration.

FIG. 4a is a section view of the wound cover of FIG. 1, taken through line 4a-4a in FIG. 2, illustrating the wound cover in the raised configuration.

FIG. 4b is a section view of the wound cover of FIG. 1, taken through line 4b-4b in FIG. 2, illustrating the wound cover in the deflated configuration.

FIG. 12 is a schematic representation the portion of the negative pressure wound therapy apparatus shown in FIG. 11, illustrating the wound cover in the semi-rigid configuration.

DETAILED DESCRIPTION OF THE PREFERRED EMBODIMENTS

Figure 1:
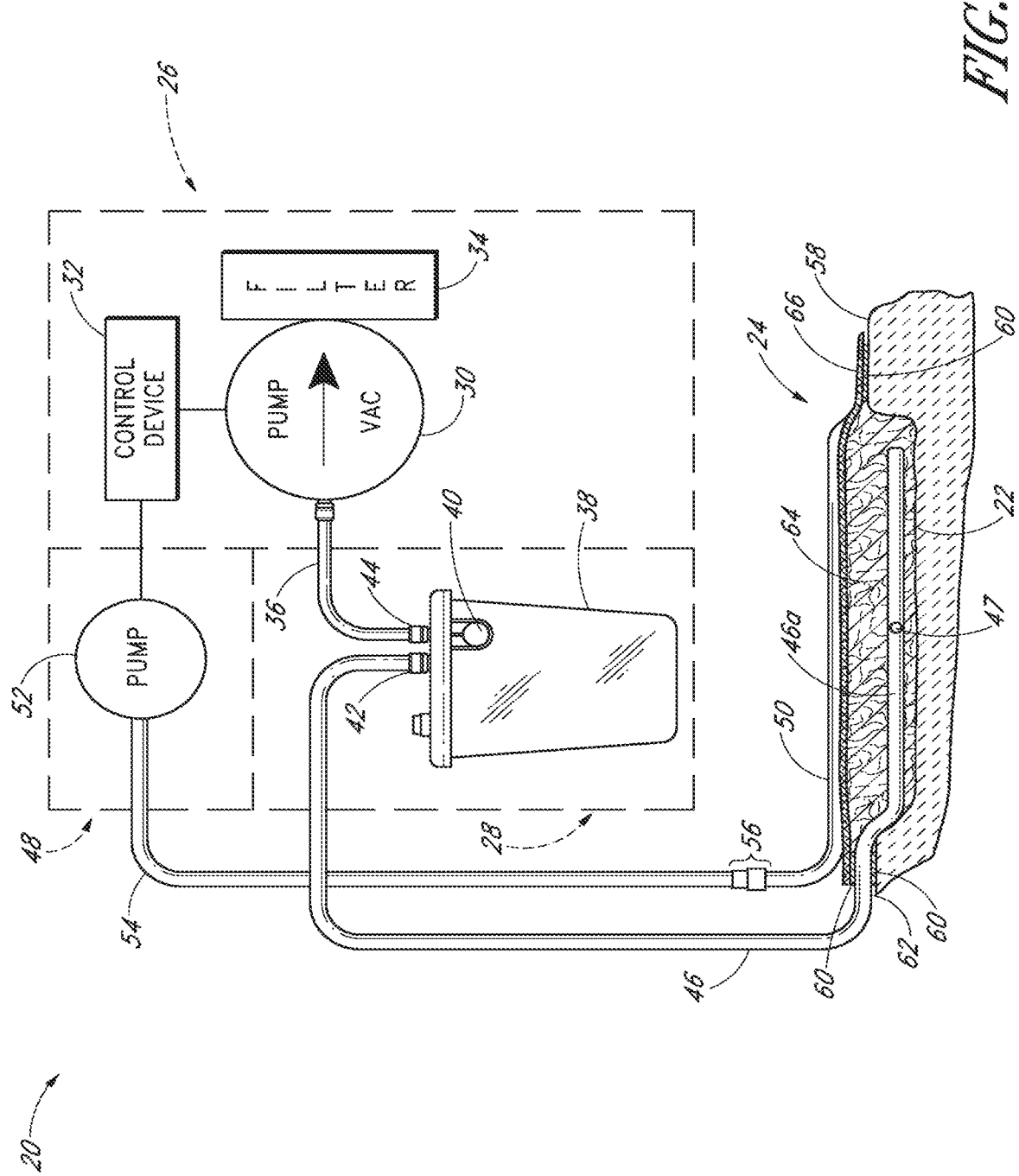
FIG. 1 is a schematic view of an embodiment of a negative pressure wound therapy apparatus, comprising an embodiment of a wound cover.

The following detailed description is now directed to certain specific embodiments of the disclosure. In this description, reference is made to the drawings wherein like parts are designated with like numerals throughout the description and the drawings.

Preferred embodiments disclosed herein relate to wound therapy for a human or animal body. Therefore, any reference to a wound herein can refer to a wound on a human or animal body, and any reference to a body herein can refer to a human or animal body. The term "wound" as used herein, in addition to having its broad ordinary meaning, includes any body part of a patient that can be treated using reduced pressure. Wounds include, but are not limited to, open wounds, pressure sores, ulcers and burns. Treatment of such wounds can be performed using negative pressure wound therapy, wherein a reduced or negative pressure can be applied to the wound to facilitate and promote healing of the wound. Additional descriptions of devices, methods and systems that can be used for wound therapy are found in U.S. Pat. No. 7,128,735 (entitled "Reduced Pressure Wound Treatment Appliance"), the entirety of which is hereby incorporated by reference and made a part of the present disclosure. It will also be appreciated that the negative pressure systems and methods as disclosed herein can be applied to other parts of the body, and are not necessarily limited to treatment of wounds.

The application of reduced or negative pressure to a wound can provide such benefits as faster healing, increased blood flow, decrease in bacterial burden, increase in the rate of granulation tissue formation, removal of exudate and slough from the wound, alleviation of interstitial edema, stimulation of the proliferation of fibroblasts, stimulation of the proliferation of endothelial cells, closure of chronic open wounds, inhibition of burn penetration, and enhancement of flap and graft attachment, among other benefits. Some or all of these benefits can be improved by the apparatus disclosed herein. Wounds that have exhibited positive response to treatment by the application of negative pressure include infected open wounds, decubitus ulcers, dehisced incisions, partial thickness burns, and various lesions to which flaps or grafts have been attached.

In particular, the embodiments disclosed herein relate to a wound cover that can be configurable so as to be either a rigid type wound cover (that can be rigid enough so as to define an air space between the wound cover and the wound) or a flexible type of wound cover (that can be collapsible so as to conform to the shape of the wound site) so as to change the volume of space between the wound cover and the wound, among other things. As will be described in greater detail below, in some embodiments, the wound cover is changed from the rigid or raised type to the flexible type by adjusting the structural rigidity and/or geometry of the wound cover. In some embodiments, the level of reduced or negative pressure applied to the wound can remain the same or substantially same (e.g., within approximately 99% to 85% of the level of applied reduced or negative pressure) when the cover is moved between the raised and collapsed configurations. Thus, the embodiments of the wound cover disclosed herein enable medical professionals to apply the rigid dome technology and/or the flexible membrane technology using the same wound cover. Further, the embodiments of the wound cover enable medical practitioners to cycle from a rigid or raised type wound cover that does not contact the wound bed or exert any physical pressure thereon, to a flexible type wound cover that can exert a small amount of physical contact pressure on the wound bed during the course of wound treatment. As will be discussed below, by allowing the wound cover to be cycled between the two types described above, the user and/or practitioner is able to optimize the negative pressure wound treatment, i.e., choose the most appropriate wound cover structure, at any point through out the healing duration In some embodiments, the wound cover is changed from a flexible type to a rigid type wound cover by providing a positive pressure to channels formed in the wound cover and, hence, inflating such channels so as to provide greater rigidity to the wound cover. In these embodiments, the wound cover will be configured such that, as the channels are inflated, the wound cover rises above the wound bed so as to form a volume of space between the wound cover and the wound bed. Thus, in these embodiments, the rigid dome technology is achieved when the wound cover is in the semi-rigid configuration, and the collapsed configuration is achieved when the wound cover is in the deflated configuration.

FIG. 1 is a schematic view of an embodiment of a negative pressure wound therapy apparatus 20, that can be configured to treat a wound by application of reduced or negative pressure (i.e., below atmospheric pressure) to a wound site 22 in a controlled manner for a predetermined amount of time. As illustrated in FIG. 1, the negative pressure wound therapy apparatus 20 can comprise a wound cover 24 (which can be referred to as a dressing) for enclosing a wound site 22 and providing a fluid-tight or substantially gas-tight enclosure over the wound site 22 to effect treatment of a wound site 22 with reduced or negative pressure. For the purpose of creating suction within the wound cover 24, the wound cover 24 is connected to a vacuum system 26 to provide a source of suction or reduced pressure for the sealed wound cover 24 at the wound site 22. Between the wound cover 24 and the vacuum system 26 is a fluid collection system 28 for intercepting and retaining exudate that is aspirated from the wound site 22. Note that, any of the materials, sizes, geometries, or other configurations or features described with respect to any wound covers in this application can be applied, as suitable, to any embodiments of the wound cover 24 disclosed herein.

Predetermined amounts of suction or reduced pressure below atmospheric pressure can be provided by the vacuum pump 30. A control device 32 can control the vacuum pump 30 so as to control the amount of suction that is provided to the wound cover 24 and wound site 22. In some embodiments, the control device 32 can be configured to operate without a processor. For example, the control circuit and other aspects of the apparatuses and methods in International Patent Application Publication No. WO2008048481, titled "Improved Control Circuit And Method For Negative Pressure Wound Treatment Apparatus," filed on Oct. 13, 2006, can be used to control the pump motor disclosed herein. Additionally, any of the configurations described in the above-mentioned WO2008048481 application regarding pressure sensors, the control of such pressure sensors, and/or other aspects of the apparatuses and methods therein can be used with the apparatus described in the present application, and International Patent Application Publication No. WO2008048481 is hereby incorporated by reference in its entirety as if fully set forth herein.

In some embodiments, the control device 32 can comprise a processor that enables the control device 32 to control the vacuum pump 30, or, as described below, the wound cover 24 or other components comprising the apparatus 20. Furthermore, the control device 32 can be a computer, data processor, or other controller having any suitable device such as, but not limited to, a processor, for controlling the pump motors and/or other components that are disclosed herein, or for receiving or changing data, or for any other function suitable for the apparatus 20.

A filter 34, such as a micropore or pathogen filter, or any other suitable component that can be configured to filter pathogenic microbes, aerosols, or other contaminants, can be attached to the exhaust of the vacuum pump 30 to prevent potentially pathogenic microbes, aerosols, or other contaminants from being vented to the atmosphere by the vacuum pump 30. In addition, a filter, such as a micropore filter, can be attached to the inlet of the vacuum pump 30, for example, at the second port 44 positioned on the top of the container 38, to prevent potentially pathogenic microbes, aerosols, or other contaminants from contaminating the wound the site 22 and/or the pump 30.

In some embodiments, the vacuum system 26 of the negative pressure wound therapy apparatus 20 can comprise two or more vacuum pumps 30 that can be connected in parallel to the collection system or wound cover 24 with tubing or conduit 36. The additional pump 30 can ensure a higher level of safety, performance, and product quality by providing pump redundancy to prevent vacuum system failure in the event that a single pump fails, in addition to more quickly and efficiently providing suction.

It should be noted that any of a wide range of vacuum pumps, pump controllers, fluid collection system, or wound packing elements or materials presently known in the art or developed in the future can be configured to be integrated into the negative pressure wound therapy apparatus 20 disclosed herein. Thus, in addition to the components and features disclosed herein, the embodiments of the negative pressure wound therapy apparatus 20 can have any of the features and components that are known in the art or that are suitable for such system. For example, one available type of apparatus that can be used to provide the necessary reduced pressure is the EZCARE Negative Pressure System available from Smith & Nephew.

As illustrated in FIG. 1, the sealed fluid collection system 28 (which can be generally gas-tight) can be comprised of a fluid-impermeable collection container 38 for containing and temporarily storing the collected exudate. The container 38 can have a shutoff mechanism 40 and can be of any size and shape suitable for intercepting and retaining a predetermined amount of exudate. The illustrated container 38 can have a first port 42 and a second port 44 positioned on the top of the container 38. The first port 42 can enable suction to be applied to the wound cover 24 through the conduit 46 and also can enable exudate from the wound site 22 to be drained into the container 38. The second port 44 can be provided to enable the application of suction from the vacuum pump 30 to the container 38 through tubing or conduit 36.

The conduit 36 and any other conduit used with the apparatus 20 or any other apparatus disclosed herein, can be sufficiently flexible to permit movement of the conduit 36 as the patient's body moves, while being sufficiently rigid to resist constriction when reduced pressure is supplied to the wound cover 24 or when an external pressure is applied to the outside of the conduit, such as from the patient or otherwise. Furthermore, the conduit 36 can have multiple chambers or lumens, or can be comprised of multiple sections of tubing that can be arranged in parallel to increase the volume of air that is supplied to or from the wound cover 24 and/or the channels 50, as is discussed below.

In some embodiments, an inflation system 48 can be configured to produce at least a source of positive pressure (i.e., above atmospheric pressure) to channels 50 of the wound cover 24 so as to controllably inflate the channels 50, as described further below. In this manner, a user or practitioner can change the wound cover 24 from a flexible type dressing or cover configuration to a rigid type dressing or cover configuration. For example, in some embodiments, a pump motor can be used to inflate a network of channels formed in the wound cover so as to increase the structural rigidity of the wound cover such that the wound cover forms a volume of space over the wound bed and is no longer in contact with the wound bed. In the semi-rigid configuration, the wound cover can be sufficiently rigid so as to not collapse when negative pressure is applied to the volume of space between the wound cover and the wound. By reducing the pressure within the network of channels 50, the wound cover 24 can be collapsed over the wound by applying a negative pressure within the volume between the wound cover and the wound. In this fashion, the wound cover can be cyclically or selectively changed from a rigid to a flexible type wound cover.

As shown in FIG. 1, the hybrid wound cover 24 is in the generally collapsed arrangement, so that it is most similar to the flexible type dressing or cover described above. As illustrated, the inflation system 48 can comprise a pressure pump 52 that is configured to supply a positive pressure to the channels 50 in the wound cover 24 through conduit 54. Similarly, to enable the wound cover 24 to change from the rigid type configuration to the flexible type configuration, the pressure pump 52 can be configured so as to reduce the pressure within the channels 50, which can be done by suctioning air from the channels 50. Thus, similar to the vacuum pump 30, the pressure pump 52 can be controlled by the control device 32 so as to control the amount of positive pressure that is supplied by the pressure pump 52 to the channels 50 of the wound cover 24, as well as to control the deflation of the channels 50 when desired. Thus, in some embodiments, the pressure pump 52 can be configured to provide a negative or reduced pressure to the channels 50. Some embodiments of the apparatus 20 further comprise pressure sensors located in the conduit 54, channels 50, or in other suitable positions to monitor the positive pressure provided by the pressure pump 52 to the channels 50 and assist with the control of the pressure pump 52.

In some embodiments, the apparatus 20 can further comprise a filter (not illustrated) that can be configured to filter the air that is supplied by the pressure pump 52 to the wound cover 24. In some embodiments, the filter can be a micropore or pathogen filter or any other suitable component that can be configured to filter pathogenic microbes, aerosols, or other contaminants from the air flowing from the pressure pump 52 to the wound cover 24 so that sterile air is provided by the pressure pump 52 to the wound cover 24. In some embodiments, this can ensure that the wound site 22 will not be exposed to any contaminants from the air supplied by the pressure pump 52 in the event that there is any leakage of air from the channels 50 into the space between the wound cover 24 and the wound site 22.

In some embodiments, the wound cover 24 and the conduit 54 can be configured to comprise a removable connector 56 so as to allow the conduit 54 to be removably connectable to the channel 50. Alternatively, the wound cover 24 can comprise one or more ports (not illustrated) for connecting the conduit 54 to the wound cover 24. Similarly, in some embodiments, the channels 50 of the wound cover 24 can comprise one or more ports (not illustrated) for connecting the conduit 54 to the channels 50.

As illustrated in FIG. 1, the wound cover 24 can be affixed to the healthy skin 58 around the periphery of the wound site 22 with adhesive 60 so as to provide a generally gas-tight or fluid-tight enclosure over the wound site 22. Note that, while a perfect seal is desirable, it is not necessary. The apparatus 20 disclosed herein can function suitably well for the intended purpose even if the seal between the healthy skin 58 and a wound cover 24 is not perfectly fluid or gas tight. In some embodiments, the wound cover 24 can be configured so as to maintain a sufficient seal between the wound cover 24 and the healthy skin 58 surrounding the wound 22 when a supply of negative pressure is provided to a wound site 22 under a wound cover 24, preferably without the application of an adhesive or other sealing member or material between the wound cover 24 and healthy skin 58 surrounding the wound 22. Thus, in some embodiments, the supply of negative pressure to the wound site 22 surrounded by the wound cover 24 can be sufficient to create a sufficiently fluid and gas tight seal between the wound cover 24 and healthy skin 58 surrounding the wound 22.

However, in some embodiments, the wound cover 24 can comprise an adhesive backing or layer 60, or other member or substance such as lanolin to facilitate the formation of a seal between the wound cover 24 and healthy skin 58 surrounding the wound site 22. In some embodiments, such substances or materials can be positioned between at least a portion of the wound cover 24 and the healthy skin 58 around wound site 22. In some embodiments, the adhesive 60 can be placed around the perimeter of the side of the wound cover 24 that will be placed against the healthy skin 58, so that he adhesive will not inadvertently come into contact with the wound site 22. The seal can be approximately gas-tight or fluid-tight over the wound site 22. The adhesive 60 can have sufficient adhesion to form a fluid-tight or gas-tight seal around the periphery of the wound site 22 and to hold the wound cover 24 in sealed contact with the skin 58 during the application of reduced pressure, as well as during application of positive pressure to the channels 50. The wound cover 24 can also provide a gas-tight seal around the conduit 46 at the feed through location 62 where the conduit 46 emerges from beneath the wound cover 24.

In some embodiments, the conduit 46 can be removably attached to the wound cover 24 through a port (not shown) positioned on the wound cover 24. In some embodiments, such a port can be integrally formed with the wound cover 24 or can be formed in a separate process and attached to the wound cover 24. In either configuration, once attached to the conduit 46, the port can provide a generally fluid-tight connection between the conduit 46 and the wound cover 24. In some embodiments, connection can be removable so that the conduit 46 can be removed from the port or the wound cover 24. Additional descriptions of wound covers comprising ports can be found in U.S. Patent Application Publication No. 2005/0261642 A1 (application Ser. No. 11/064,813), titled "Flexible Reduced Pressure Wound Treatment Appliance" and filed on Feb. 24, 2005, the entirety of which is hereby incorporated by reference and made a part of the present disclosure as if fully set forth herein.

As discussed above, some embodiments of the apparatus 20 and wound cover 24 can be configured so as to not require any adhesive to provide a sufficiently fluid-tight seal between wound cover 24 and the healthy skin 58 surrounding the wound. In these embodiments, the wound cover 24 can be configured such that the application of negative pressure to the wound site 22 creates a sufficient seal between the wound cover 24 and the patient's body so as to maintain a sufficiently fluid and gas tight seal over the wound site 22. Additionally, in some embodiments, other substances that promote a sufficiently fluid-tight seal without having adhesive effects, such as Lanolin or any other suitable substance, can be used.

In some embodiments, the apparatus 20 can also comprise a suction drain positioned within or adjacent to the wound site 22. The suction drain can comprise a bottom drain portion (such as, but not limited to, a tube segment 46a described below and illustrated in FIG. 1) extending into the wound site 22 under the wound cover 24. The drain portion can be attached to the end of the tube 46 and can be comprised of polymer tubing that is flexible enough to allow the tube to easily bend, but rigid enough to prevent the conduit from collapsing during use. In other embodiments, portions of the drain portion can be comprised of other materials, such as flexible or semi-rigid polymers, plastics, rubber, silicone, or combinations of such materials. In yet other embodiments, the drain portion can have different cross-sectional shapes, such as elliptical, square, rectangular, pentagonal, hexagonal, or other shapes. Additionally, in some embodiments, the drain portion can have openings or perforations along a portion of the length thereof through which exudate or other material that is removed from the wound site 22 can pass.

In some embodiments, as in the embodiment illustrated in FIG. 1, the apparatus 20 can also comprise an absorbable matrix 64 or other wound packing material such as gauze (non-adherent, anti-microbial, or otherwise), open cell foam, sea sponges, or other suitable or desirable objects or materials that can allow the transmission of suction within the wound site 22. In further embodiments, the matrix can be non-bioabsorbable, as is known in the art. In the illustrated embodiment, the tube segment 46a embedded within the absorbable matrix 48 can have at least one side port 47 positioned within the interior of the absorbable matrix 64 to enable a substantially uniform application of reduced pressure throughout the enclosure. In other embodiments, the tube segment 46a can comprise a plurality of side ports 47 positioned within the interior of the absorbable matrix 64. The absorbable matrix 64 can be comprised from any material suitable for negative pressure wound therapy, such as is described in U.S. Patent Application Publication No. US 2004/0073151 A1, titled "Reduced Pressure Wound Treatment Appliance," which is hereby incorporated by reference in its entirety as if fully set forth herein. Embedding the open end of segment 46a of tube 46 within the interior of the absorbable matrix 64 can permit the absorbable matrix 64 to function as a shield to help prevent the wound cover 24 from being inadvertently sucked into sealing engagement with the open end of the tube, which can plug the tube 46 and restrict the flow of reduced pressure to the wound cover 24. In addition, the absorbable matrix 64 can encourage the growth of tissue in the area of the wound 22 into the matrix 64 and can hold the wound cover 24 generally out of contact with the wound 22 during the application of suction to the enclosure.

Figure 2:
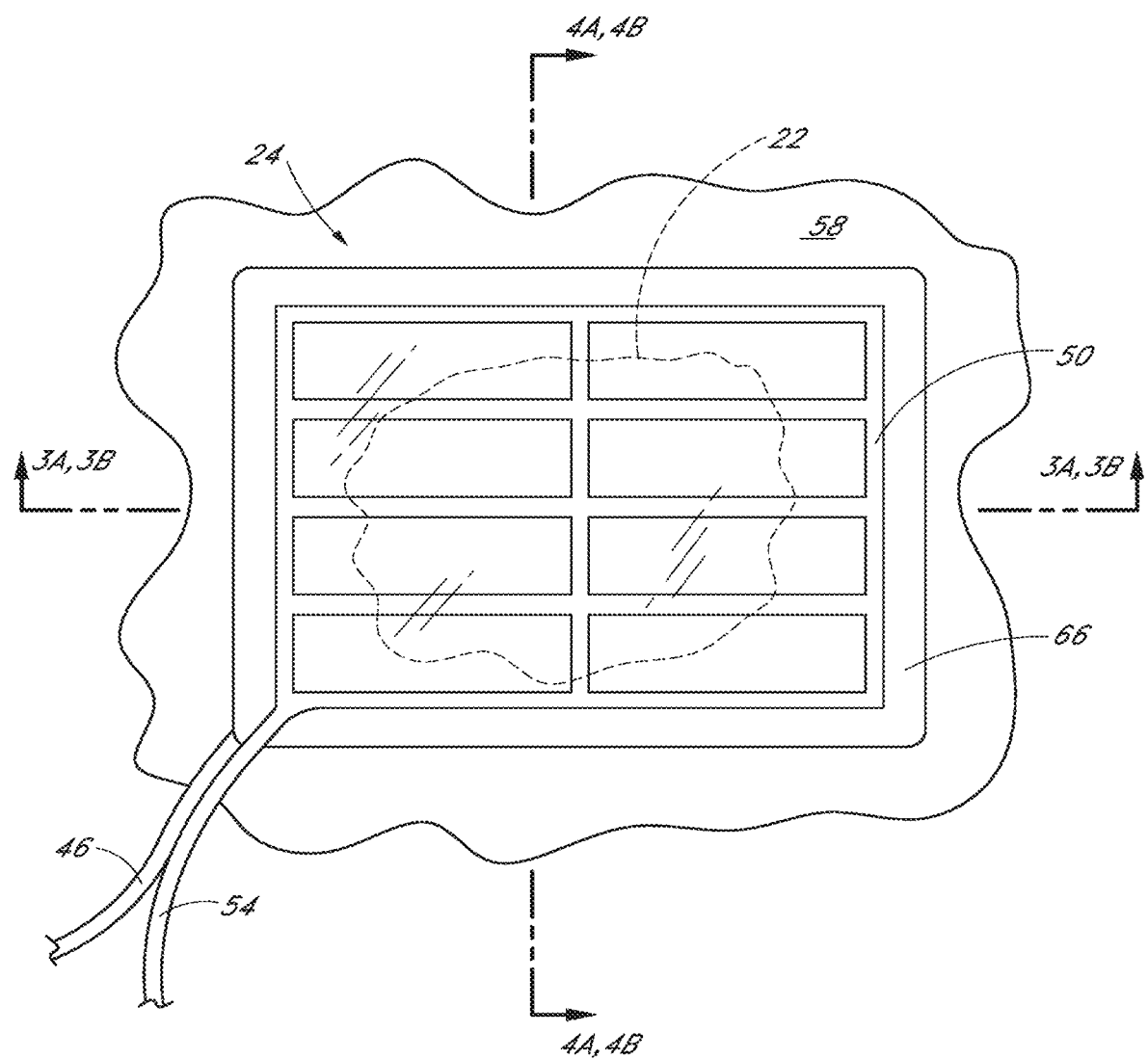
FIG. 2 is a top view of a portion of an embodiment of a collection system.

FIG. 2 is a top view of an embodiment of the wound cover 24. As illustrated in FIG. 2, the wound cover 24 can be positioned over the wound site 22 such that the adhesive 60 on the wound cover 24 adheres the wound cover 24 to the healthy skin 58 surrounding the wound site 22. As illustrated in FIG. 2, the conduit 54 can be interconnected with the channels 50 so as to be a fluid communication with the channels 50. In some embodiments, the conduit 50 can be connected to the channels 50 using a typical connector (not illustrated) of the type found in the field. In some embodiments, the wound cover 24 can be formed so that a predetermined length of conduit 54 is integrally formed with the channels 50 on the wound cover 24. In such embodiments, the predetermined length of conduit 54 provided with the wound cover 24 can be long enough so as to be interconnectable with the pressure pump 52.

As shown in FIG. 2, the channels 50 of this embodiment can be arranged in a rectangular fashion so as to define a plurality of rows. In the illustrated arrangement, the wound cover 24 can comprise five rows of channels 50 arranged in a direction that is parallel with the line 3A-3A, and three rows of channels 50 arranged in a direction that is parallel with the line 4A-4A. However, the wound cover 24 is not limited to this arrangement, but can define any number of rows of channels 50 suitable for the size of the wound cover 24, the size of the wound, the location of the wound on the body, the desired amount of rigidity of the wound cover 24 when it is in the raised position or configuration, or any other characteristics related to the performance of the wound cover 24. The wound cover 24 can be formed in any of a wide range of sizes and shapes so that a particularly beneficial size of the wound cover 24 is available for any wound in a wide range of sizes, shapes, and locations on the body.

In some embodiments, the wound cover 24 can comprise a greater or lesser number of rows of channels 50 in either direction as compared to the embodiments illustrated or described herein. For example, in some embodiments, the wound cover 24 can have an approximately square perimeter and comprise six or more rows of channels 50 arranged in a direction that is parallel with the line 3A-3A, and six or more rows of channels 50 arranged in a direction that is parallel with the line 4A-4A. Additionally, in some embodiments, the channels can be arranged in any suitable geometric pattern. For example, without limitation, the channels 50 can be interconnected so as to efficiently allow air to flow into and out of all of the channels 50. In some embodiments, the wound cover 24 and channels 50 (or any wound cover or channel configuration disclosed herein) can define a square, circular, triangular, or ovular shaped, or any other desired or suitable shape.

In some embodiments, the channel or channels 50 can cover approximately the entire cover or approximately the entire wound bed. In some embodiments, the cover can have only one substantially enclosed channel or pocket that covers approximately all of the wound cover 24 and/or wound bed, with the only opening(s) therein being in the one or more ports or one or more other openings that allow air to flow from the air pressure supply conduit(s) into or out of the channel or pocket (but, otherwise, the channel or pocket can be fully enclosed). In some embodiments, the substantially enclosed channel or pocket can be formed between two layers of impermeable or semi-impermeable material comprising the wound cover 24, the two layers being laminated or otherwise sealingly joined around the periphery thereof. The two layers can have internal walls, connections, or other features configured to provide one or more connection points between the two layers within the periphery of the two layers.

Additionally, in some embodiments, the shape of the wound cover 24 can be different than the shape of the network of channels 50. For example, without limitation, the wound cover 24 can define a square or circular perimeter, whereas the channels 50 can form a crisscross pattern on the wound cover 24, or any other pattern suitable to allow the wound cover 24 to preferably to change between the raised (or rigid) and collapsed (or flexible) configurations.

In general, the channels 50 can be configured and arranged on the wound cover 24 so as to provide the wound cover 24 with a desired shape or to allow the wound cover 24 to take a desired shape, both in the rigid configuration or position and of the collapsed configuration or position. The channels 50 can be configured so as to define any suitable cross-sectional shape when the channels 50 are in a generally inflated configuration or state. For example, in some embodiments, the channels can define a round, ovular, triangular, square, rectangular, pentagonal, or other suitable shape. Further, the wall thickness of the material forming a walls of the channels 50 can be selected or determined based on factors such as, but not limited to, the material used to form the channels 50, the shape of the wound cover 24, the contour of the skin that the wound cover 24 is to be adhered to, the desired amount of rigidity of the wound cover 24 in the dome configuration or position, the desired amount of flexibility of the wound cover 24 in the collapsed configuration or position, or other factors. In some embodiments, the channels 50 can be configured such that, when the channels 50 are deflated, the deflated channels 50 are sufficiently compliant so that the wound cover 24 can conform to the wound site 22 or any wound packing materials placed in the wound site 22, while being sufficiently rigid so as to position wound cover 24 in the dome or raised position when the channels 50 are inflated.

FIG. 3A is a section view of the wound cover 24 illustrated in FIG. 2, taken through line 3a-3a in FIG. 2, illustrating an embodiment of the wound cover 24 in the raised or rigid configuration (also referred to herein as the raised or rigid dome position, or raised position). FIG. 4a is a section view of the wound cover 24 taken through line 4a-4a in FIG. 2, also illustrating an embodiment of the wound cover 24 in the raised configuration. In the illustrated configuration, the wound cover 24 can comprise a flexible sheet member 66 and at least one channel 50 formed on, or adhered to, the top surface of the flexible sheet member 66. The at least one channel 50 can also be integrally formed with the flexible sheet member 66. The wound cover 24 can be configured to generally maintain a reduced pressure in the space 68 when suction is applied to the space 68.

In some embodiments, the sheet or member 66 can be sized and configured to be placed over and enclose the wound 22 so as to define a space 68 between the flexible sheet member 66 and the wound 22 when the wound cover 24 is in the raised configuration. In some embodiments, the member 66 (that can be flexible) illustrated in FIG. 3A, or any flexible member of any embodiment of the wound cover disclosed herein, can be sized and configured so as to be generally unstretched when the flexible membrane is in the raised configuration, as illustrated in FIG. 3A. In particular, in some embodiments, the flexible sheet member 66 can be sized and shaped so as to define a concave and/or convex shape when the flexible sheet member 66 is in an unstretched state. In this configuration, because the member 66 preferably does not have to be stretched when the wound cover is changed from the collapsed configuration to the raised configuration, a smaller force can be required to be exerted by the channels 50 on the member 66 to raise the member 66 to the raised configuration. Additionally, in this configuration, the wound cover 24 can be better arranged to conform to any depressions in the wound bed. As a result, the wound cover can be more easily changed from the collapsed configuration to the rigid, raised configuration, and will be better equipped to create an airspace between the wound cover and the wound bed in the arranged configuration, and the better equipped to conform to the wound bed and the flexible configuration.

In the embodiment of the wound cover 24 wherein the wound cover 24 is in the raised or rigid configuration, as illustrated in FIG. 3a, a positive supply of pressure has preferably been supplied by the pressure pump 52 to the channels 50 of the wound cover 24 so as to cause the wound cover 24 to rise above the wound site 22 and create a space 68 between the wound cover 24 and the wound site 22. As can be seen in FIG. 3a, a series of openings 50a can interconnect the channels 50 so that the channels 50 form a continuous network. As mentioned, in the illustrated embodiment, the channels 50 can be formed on the top, outer surface of the flexible sheet or member 66. However, the wound cover 24 is not limited to this configuration. The channels 50 and wound cover 24 can be of any suitable size or configuration, or located at any suitable position to selectively provide rigid support to an otherwise generally flexible wound cover 24, so as to selectively cause the wound cover 24, to be raised above the wound site 22 when desired. In the raised configuration, the wound cover 24 can be sufficiently rigid to withstand collapse or buckling, so as to maintain the volume of space 68 between the member 66 and the wound site 22 when negative pressure is supplied to the wound site 22 through conduit 46.

In any embodiments disclosed herein, the channels 50 can be sized, structured, or otherwise configured to have a pre-memorized shape or curvature that can bias the wound cover 24 to a dome type configuration or position wherein the volume of space is created between the wound cover 24 and the wound site 22 when the channels 50 are inflated or otherwise activated. Conversely, in some embodiments, the channels 50 can be sized, structured, or otherwise configured so that, when the positive pressure has been generally removed from the channels 50, the channels 50 do not bias the wound cover 24 to a dome type configuration or position but, rather, allow the wound cover 24 to conform to the shape of the wound site 22 and/or the wound packing material that is in the wound site 22. Accordingly, in some embodiments, when the positive pressure has been generally removed from the channels 50, the channels 50 can appear crumpled or otherwise unstretched.

FIG. 3b is a section view of the wound cover 24 illustrated in FIG. 1, taken through line 3b-3b in FIG. 2, illustrating an embodiment of the wound cover 24 in the deflated or collapsed configuration (also referred to herein as the deflated or collapsed position) wherein the wound cover 24 most closely resembles a flexible membrane wound cover. FIG. 4b is a section view of the wound cover 24 taken through line 4b-4b in FIG. 2, also illustrating an embodiment of the wound cover 24 in the deflated configuration. In the deflated configuration of the embodiment illustrated in FIG. 3b, the channels 50 can be deflated so that they no longer rigidly support the wound cover 24 over the wound site 22. Thus, in this configuration, the channels 50 can be flexible enough so that they do not substantially impede the flexibility of the wound cover 24. Accordingly, the supply of negative pressure via conduit 46 can cause the wound cover 24 to flexibly collapse over the wound site 22, as is also illustrated in FIG. 1. Additionally, as discussed above and shown in FIG. 1, a wound packing material such as gauze or an absorbable matrix can be positioned over the wound site 22, below the wound cover 24. When such wound cover is included, the wound cover 24 can be configured to flexibly collapse over such wound packing material.

As illustrated in FIGS. 2-4B, the thickness of each of the walls of the channels 50 can be designed so that the channels 50 can be flexible when the channels 50 are deflated, as shown in FIG. 3B, but sufficiently rigid to support the wound cover 24 when the channels 50 are inflated. Further, in the embodiment illustrated in FIG. 2, the channels 50 can be arranged on the flexible sheet 66 in a rectangular shape such that the channels 50 form a perimeter shape that matches, but is slightly undersized as compared to, the perimeter of the flexible sheet 66. As described above, the internal openings 50*a*, 50*b* can create a network of internal air passageways that allow the air supply through the conduit 54 to preferably completely fill all the channels 50 in an efficient manner. In some embodiments, the channels 50 can be formed such that the internal air space 50*a* is greater near the middle of the channel 50 than at the end portion of the channel 50, i.e., such that internal height of the channels 50 (represented by the dimension "t" in FIG. 3A) is greater near the middle portion of the channels 50 than at the end portions of the channel 50. This can provide greater structural rigidity to the wound cover 24, when the channels 50 are in the inflated configuration.

As stated above, in some embodiments, when the channels 50 are deflated, such as is illustrated in FIG. 3B, the material comprising the channels 50 can be unstretched and somewhat crumpled, such as in an accordion-like fashion (not shown). In this configuration, the channels 50 and the wound cover 24 can be more flexible and pliable, so that the negative pressure supplied to the space 68 will cause the wound cover 24 to be drawn toward the wound site 22. When such channels 50 are inflated, the material comprising the channels 50 can then be expanded and stretched, which can bias the wound cover 24 to the expanded or raised configuration or position.

In some embodiments, the apparatus 20 can be configured so that, before the wound cover 24 is changed from the collapsed configuration to the raised configuration, a positive pressure is supplied for a short duration of time to the volume of space 68 between the wound cover 24 and the wound site 22. The positive pressure supplied to the space 68 will help ensure that, as the pressure within the channels 50 is being increased and, hence, the wound cover 24 is becoming more rigid, the wound cover 24 expands to form a rigid enclosure over the wound site 22 so as to increase the volume of space 68 over the wound site 22 instead of buckling against the wound site 22. After the channels 50 have been sufficiently pressurized so as to form a rigid wound enclosure 24, the pressure within the space 68 can then be reduced to a level that is beneficial to the healing of the wound site 22. This positive pressure loading can have other benefits also. In other embodiments, the size and geometric configuration of the channels 50 will help ensure that, as the channels 50 are being pressurized, the wound cover 24 expands upwardly away from the wound site 22, despite the magnitude of negative pressure that can be present in the volume of space 68.

The channels 50 can be formed integrally with the member 66, or can be formed in a separate process and bonded with adhesive to, fused with, or otherwise adhered to the outer surface of the member 66. In some embodiments, the channels 50 can be positioned or formed on the inside surface of the member 66 so as to be within the interior space 68 between the member 66 and the wound bed 22. In some embodiments, the member 66 can be formed between symmetrical, opposing channels 50. In some embodiments, as in the illustrated embodiments the member 66 can be formed around the outside perimeter of the network of channels 50 so as to form a perimeter around the channels 50 that can be bonded to the healthy skin 58 surrounding the wound 22.

The channels 50 and/or member 66 of the wound cover 24 can comprise any suitable medical grade flexible material that is currently known in the art or that may be developed in the art in the future. Such material can be fluid-impermeable or semi-permeable and otherwise suitable for purposes of wound treatment (e.g., can be sterilized or cleaned and does not absorb significant amounts of wound exudate), and is capable of forming an approximately liquid and/or fluid and gas tight seal with the surface of the skin around the site of the wound, as is discussed above. In some embodiments, the wound cover 24 can be formed from polyurethane. In some embodiments, the wound cover 24 can be formed from materials such as, but not limited to, rubber including neoprene, and/or flexible polymer materials such as silicone, silicone blends, silicone substitutes, polyester, vinyl, polyimide, polyethylene napthalate, polycarbonates, polyester-polycarbonate blends, polyurethane, ethyl vinyl acetate, or any other similar or suitable polymer or combinations of all such materials. The channels 50 can be formed from any of the materials comprising the member 66, or any other suitable material.

Figure 5:
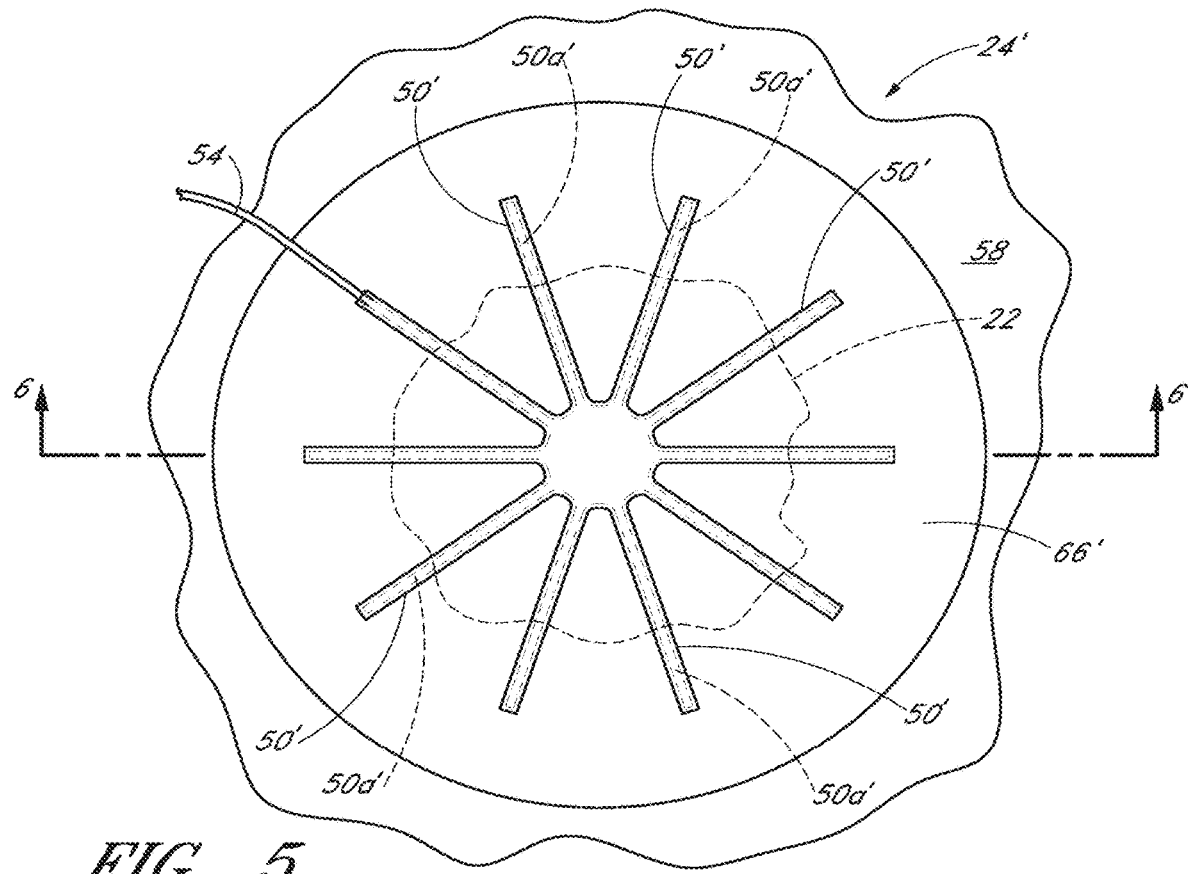
FIG. 5 is a top view of another embodiment of a wound cover.
Figure 6A:
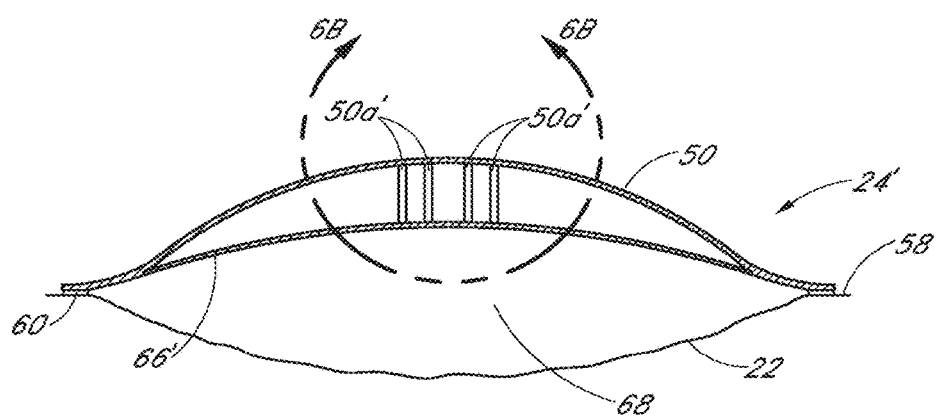
FIG. 6A is a section view of the wound cover of FIG. 5, taken through line 6A-6A in FIG. 5, illustrating the wound cover of FIG. 5 in the rigid or raised configuration.
Figure 6B:
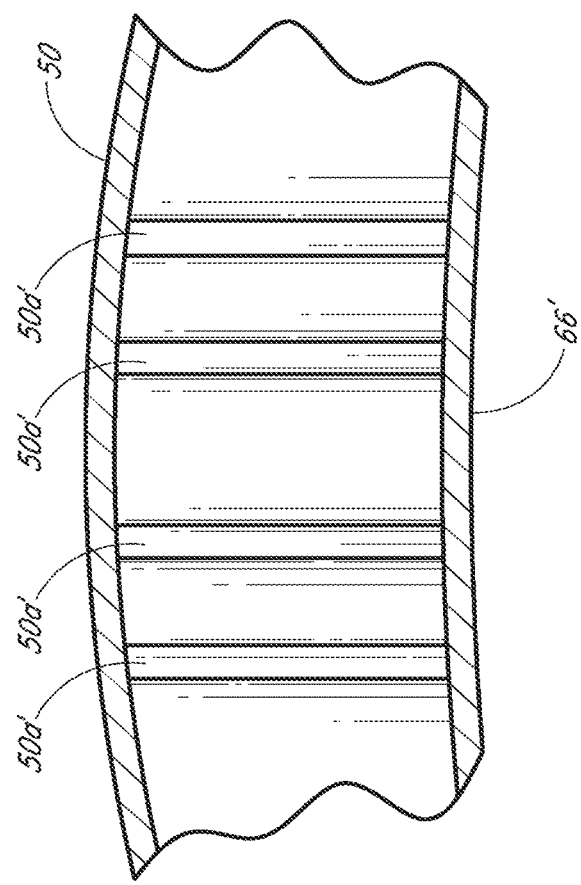
FIG. 6B is an enlarged section view of a portion of the wound cover of FIG. 5, defined by curve 6B-6B in FIG. 6A.

FIG. 5 is a top view of another embodiment of a wound cover 24', and FIG. 6A is a section view of the wound cover 24' taken through line 6-6 in FIG. 5, illustrating the wound cover 24' in the rigid or raised configuration. FIG. 6B is an enlarged section view of a portion of the wound cover of FIG. 5, defined by curve 6B-6B in FIG. 6A. Any of the materials, sizes, geometries, or other configurations or features described with respect to other wound covers in this application can be applied, as suitable, to any embodiments of the wound cover 24' disclosed herein. In the illustrated configuration, the wound cover 24' can be integrally formed such that the channels 50' and the member 66' (that can be flexible) are formed from a single piece of material or from two or more separate materials formed in the same process so as to be seamlessly joined. However, the embodiment of the wound cover 24' illustrated in FIGS. 5 and 6 is not so limited. In some embodiments, the channels 50' could be formed in a separate process as compared to the member 66' and adhered or bonded to, or otherwise attached to, the member 66'. In the illustrated embodiment, the openings 50*a*' can allow the positive pressure provided by the conduit 54 to travel through the wound cover 24' and fill all of the channels 50'.

In the illustrated embodiment, as positive pressure can be provided through conduit 54 to the channels 50', the channels 50' can be caused to expand. The channels 50' can be configured such that, as they expand, they cause the bottom surface of the member 66' to rise above and move away from the wound site 22. In the illustrated embodiment, the channels 50' can be relatively tall in profile (as best illustrated in FIG. 6A, 6B), so as to provide a substantial amount of structural rigidity to the wound cover 24' to keep the wound cover 24' from collapsing on the wound site 22 as negative pressure is being provided to the volume of space 68 between the wound cover 24' and the wound site 22. Additionally, in the illustrated embodiment, the channels 50' can be relatively narrow in width so as to minimize the total volume of the channels 50' so that the channels 50' can be quickly inflated and deflated to change the wound cover 24' between a rigid and flexible type cover. Additionally, the channels 50' and other components comprising the wound cover 24' can be configured such that, as the pressure is removed from within the channels 50', the wound cover 24' become sufficiently flexible so as to collapse over the wounds 22 when a negative pressure is supplied to the volume of space 68 between the wound cover 24' and the wound 22.

Figure 7:
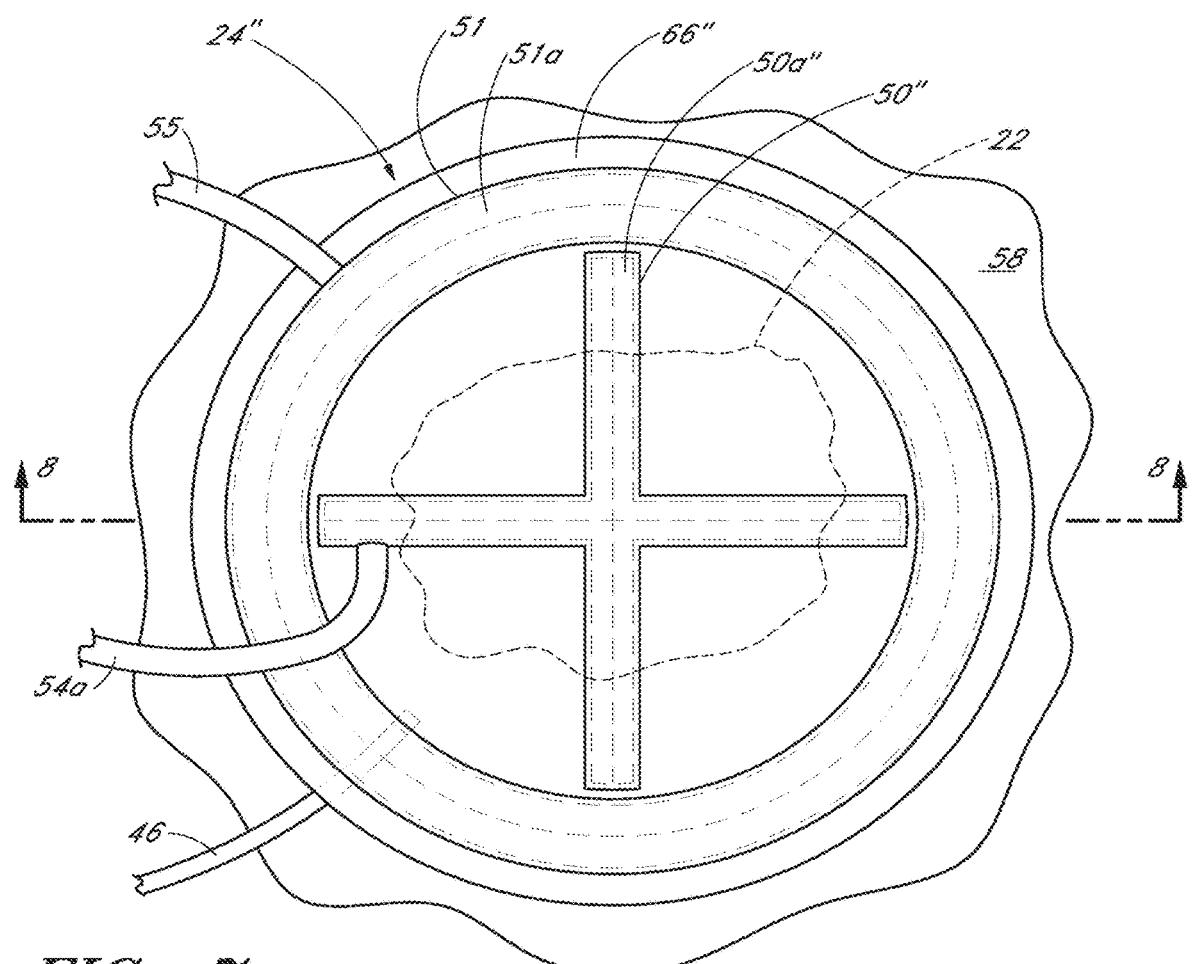
FIG. 7 is a top view of another embodiment of a wound cover.
Figure 8:
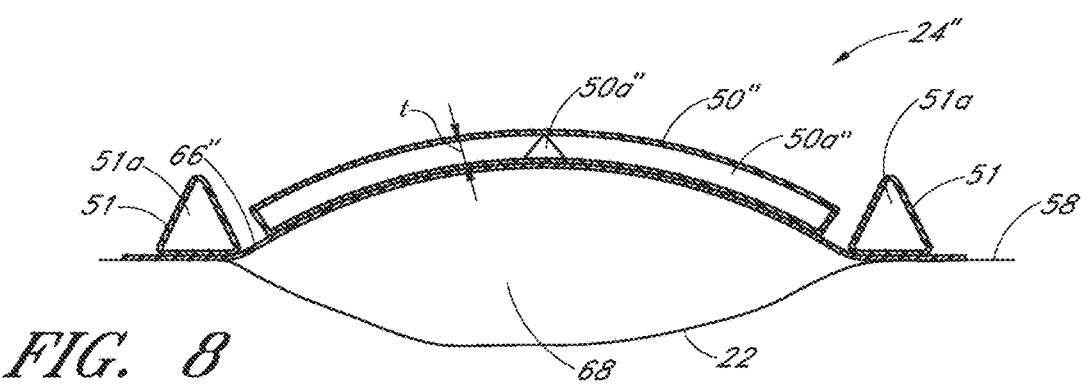
FIG. 8 is a section view of the wound cover of FIG. 7, taken through line 8-8 in FIG. 7, illustrating the wound cover of FIG. 7 in the raised configuration.

FIG. 7 is a top view of another embodiment of a wound cover 24", and FIG. 8 is a section view of the wound cover 24" taken through line 8-8 in FIG. 7, illustrating the wound cover 24" in the rigid or raised configuration. Any of the materials, sizes, geometries, or other configurations or features described with respect to other wound covers in this application can be applied, as suitable, to any embodiments of the wound cover 24″ disclosed herein. In the illustrated embodiment, the channels 50″ can be formed separately as compared to the member 66″ (that can be flexible) and can be adhered to or otherwise joined to the member 66″ by any suitable method. However, the embodiment of the wound cover 24″ illustrated in FIGS. 7 and 8 is not so limited. In some embodiments, the channels 50″ can be integrally formed with the member 66″ so that the channels 50″ and the member 66″ are formed from a single piece of material or from two or more separate materials formed in the same process so as to be seamlessly joined.

In some embodiments, the sheet or member 66″ can be sized and configured to be placed over and enclose the wound 22 so as to define a space 68 between the flexible sheet member 66″ and the wound 22 when the wound cover 24″ is in the raised configuration. In some embodiments, the member 66″ illustrated in FIG. 8, or any flexible member of any embodiment of the wound cover disclosed herein, can be sized and configured so as to be generally unstretched when the flexible membrane is in the raised configuration, as illustrated in FIG. 8. In particular, in some embodiments, the flexible sheet member 66″ can be sized and shaped so as to define either a concave or convex shape when the flexible sheet member 66″ is in an unstretched state. In this configuration, because the member 66″ preferably does not have to be stretched when the wound cover is changed from the collapsed configuration to the raised configuration, a smaller force can be required to be exerted by the channels 50″ on the member 66″ to raise the member 66″ to the raised configuration.

In some embodiments, as in the illustrated embodiment, the channels 50″ can define a generally triangular shaped cross-section and are positioned on the member 66″ in a generally crisscross pattern. However, the shape and positioning of the channels 50″ is not limited to the shape and positioning shown in FIG. 7. The wound cover 24″ can be configured such that the channels 50″ define any suitable shape and are positioned at any suitable position on the wound cover 24″. In some embodiments, the channels in this or any other embodiment disclosed herein can define a semi-circular, triangular, square, rectangular, or any other suitable cross-section. As with the embodiments described above, the openings 50a″ can be configured to allow the positive pressure, that can be provided by the conduit 54, to flow through the wound cover 24″ so as to fill all of the channels 50″. Additionally, as seen most clearly in FIG. 8, the height of the channels 50″ (represented by "t" in FIG. 8) can be uniform across the entire length of the channels 50″. In some embodiments, the height of the channels 50″ can be varied across the entire length of the channels 50″. For example, in some embodiments, the channels 50″ can be tapered such that the height t of any of the channels 50″ is greatest near the center of the wound cover 24″ and less near the periphery of the wound cover 24″.

In the illustrated embodiment, as positive pressure is provided through conduit 54 to the channels 50″, the channels 50″ can be caused to expand. The channels 50″ can be configured such that, as they expand, they cause the bottom surface of the member 66″ to rise above and move away from the wound site 22. In the illustrated embodiment, the channels 50″ can be relatively tall in profile (as best illustrated in FIG. 8) so as to provide a substantial amount of structural rigidity to the wound cover 24″ to keep the wound cover 24″ from collapsing on the wound site 22 as negative pressure is being provided to the volume of space 68 between the wound cover 24″ and the wound site 22. Additionally, in the illustrated embodiment, the channels 50″ can be relatively narrow in width so as to minimize the total volume of the channels 50″ so that the channels 50″ can be quickly inflated and deflated to change the wound cover 24″ between a rigid and flexible type cover. Additionally, the channels 50″ and other components comprising the wound cover 24″ can be configured such that, as the pressure is removed from within the channels 50″, the wound cover 24″ can become sufficiently flexible so as to collapse over the wounds 22 when a negative pressure is supplied to the volume of space 68 between the wound cover 24″ and the wound 22.

Additionally, as illustrated in FIGS. 7 and 8, in some embodiments, the wound cover 24″ can comprise a peripheral channel 51 that can be positioned so as to be adjacent to the perimeter of the wound cover 24″. The peripheral channels 51 can be configured to be inflated and deflated with conduit 55, and to define an inner airspace 51a. The peripheral channel 51 can be configured so as to be separate from the channels 50″ so as to define a separate airspace. In this arrangement, the inflation and deflation of the peripheral channel 51 can be controlled independently from the inflation and deflation of the channels 50″. However, in some embodiments, the peripheral channel 51 can be configured so as to be and fluid communication with the channels 50″.

In some embodiments, the peripheral channel 51 can be sized, positioned, and configured so as to selectively increase the structural rigidity of the peripheral edge of the wound cover 24″, so that the peripheral portion of the wound cover 24″ is biased to conform to the shape of the inflated peripheral channel 51. Therefore, in some embodiments, when the peripheral channel 51 is inflated, the wound cover 24″ can be better equipped to be sealed to the healthy skin 58 surrounding the wound site 22 without the use of an adhesive or other sealing material or component.

As illustrated in FIG. 8, the peripheral channel 51 can be formed from any of the materials disclosed above for any components of the wound cover 24 or channels 50. In some embodiments, the peripheral channel 51 can be formed from the same material used to form the channels 50″ and can comprise a similar cross-section as the cross-section of the channels 50. In some embodiments, the peripheral channel 51 can define a semi-circular, triangular, square, rectangular, or other suitably shaped cross-section. In the illustrated embodiment, the peripheral channel 51 can define a triangular cross-section. The peripheral channel 51 can also be formed integrally with the flexible sheet member 66″, or can be formed separately and adhered to, laminated to, or otherwise attached to or supported by the flexible sheet member 66″. The peripheral channel 51 can be configured to work with any of the wound covers disclosed herein, including the square, rectangular, ovular, or other shaped wound covers 24 disclosed herein.

In some embodiments, the wound cover 24″ or any wound cover disclosed herein can be configured so that a peripheral portion of the wound cover is structurally supported in a different manner than as described above so as to maintain a desired shape even when channels 50 are deflated. For example, in some embodiments, a rigid or semi-rigid band of material can be supported by or attached to the wound cover 24 adjacent to or close to the peripheral edge of the wound cover 24 in place of the peripheral channel 51. The rigid or semi-rigid band of material can be configured to increase the rigidity of the peripheral portion of the wound cover 24 so that the wound cover 24 can maintain a desired shape based on the shape of the band of such material. In some embodiments, the band of material can be bendable or otherwise moldable so that a medical practitioner or user can shape the band of material to approximately match the contour of the patient's body adjacent to the wound site. In such embodiments, the material can be configured to retain its shape after being bent or molded so that the shape of the band of material and the peripheral edge of the wound cover approximately match the contour of the patient's body adjacent to the wound site. Additionally, these embodiments can be configured so that a supply of negative pressure through the conduit 46 to the volume of space 68 between the wound cover 24 and the wound site 22 create a suction seal between the wound cover 24 and the healthy skin 58 adjacent to the wound site 22. In other words, in some embodiments, the supply of negative pressure to the wound cover 24 can exert an adequate pressure on the wound cover 24 so as to sufficiently seal the wound cover 24 to the patient's body without the use of an adhesive or other sealing material.

Some embodiments of the negative pressure wound therapy apparatus 20 can be configured so that the wound cover 24 can be changed from the semi-rigid or raised configuration (i.e., the configuration shown in FIGS. 3*a*, 4*a*, and 5) to the collapsed configuration (i.e., the configuration shown in FIGS. 3*b*, and 4*b*) by methods and/or techniques other than through adjusting the air pressure of portions of the wound cover 24 as described above. For example, in some embodiments, one or more strips of piezoelectric material or other length changing material (i.e., material that changes length when, for example, but not limited to, heat or an electrical current is applied to such material) can be supported by, laminated to, or formed within a portion of the flexible sheet member 66 of the wound cover. In these embodiments, the end portions of the length changing material or member can be supported and/or such material or member can be configured so that at least the middle portion of the length changing material or member would bend away from the wound site when the length of such material or member is increased. In some embodiments, the wound cover can be configured so that, when the strip or strips of length changing material are bent upward, the flexible sheet member 66 which sealably encloses the wound site 22 can be displaced upwardly.

Figure 9:
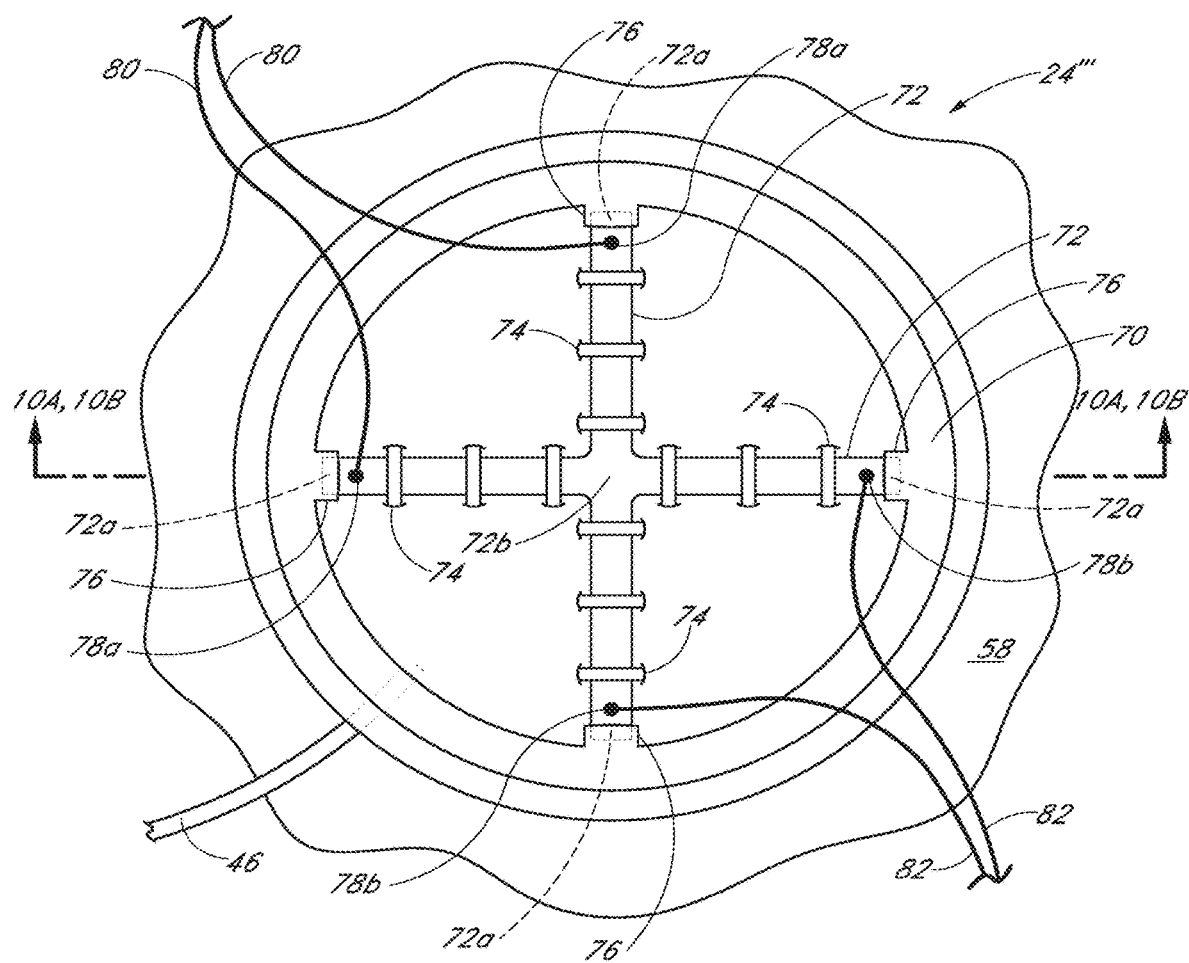
FIG. 9 is a top view of another embodiment of a wound cover.
Figure 10A:
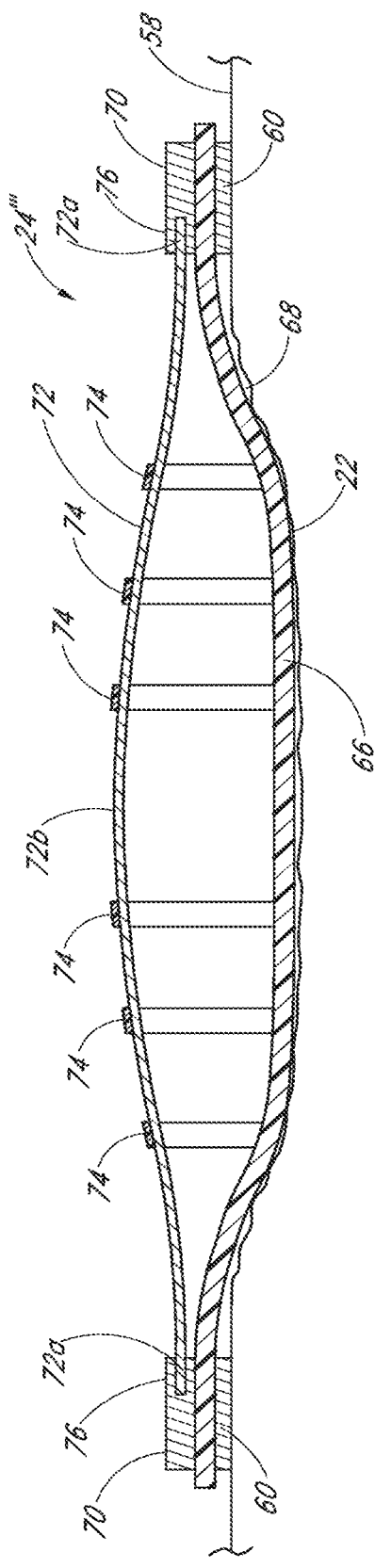
FIG. 10A is a section view of the wound cover of FIG. 9, taken through line 10A-10A in FIG. 9, illustrating the wound cover of FIG. 9 in the collapsed configuration.
Figure 10B:
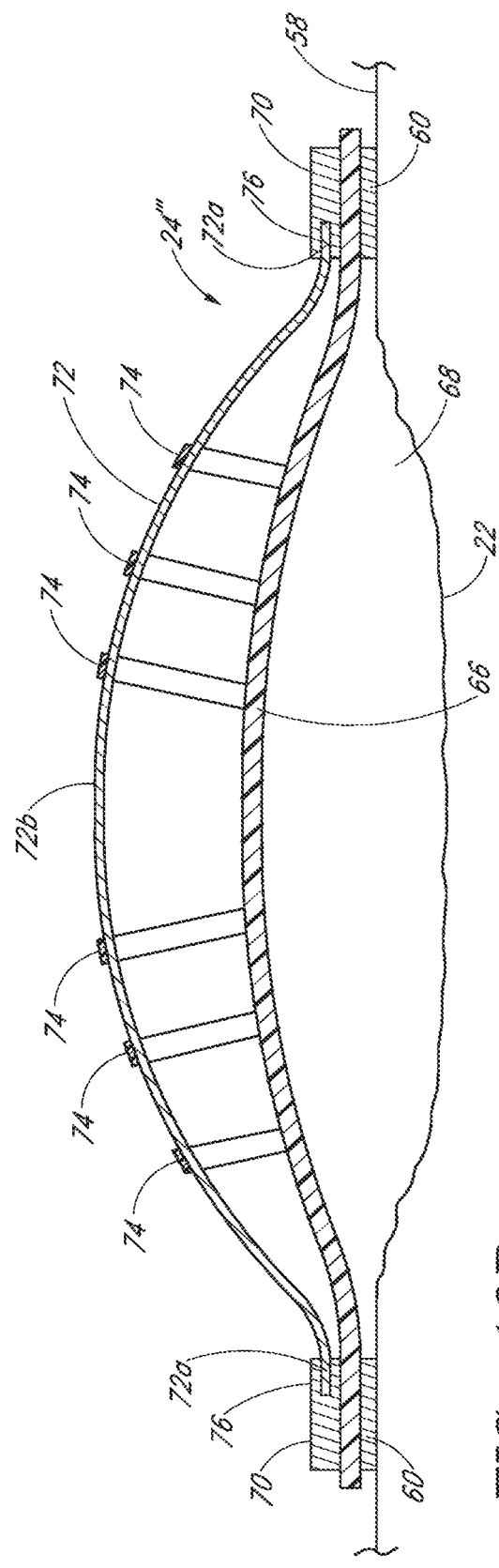
FIG. 10B is a section view of the wound cover of FIG. 9, taken through line 10B-10B in FIG. 9, illustrating the wound cover of FIG. 9 in the raised configuration.

FIG. 9 is a top view of an embodiment of a wound cover 24''' comprising a length changing member. In some embodiments, the length changing member can be formed from a piezoelectric material. In some embodiments, the length changing member can be formed from a material that changes length in response to a thermal energy (i.e., heat) being supplied to the length changing member. FIG. 10A is a section view of the wound cover 24''', taken through line 10A-10A in FIG. 9, illustrating the wound cover 24''' in a collapsed position or configuration. FIG. 10B is a section view of the wound cover 24''', taken through line 10B-10B in FIG. 9, illustrating the wound cover 24''' in a raised position or configuration. As mentioned, in some embodiments, the length changing member can be formed from a material that changes length in response to heat or thermal energy being applied to the material, or can be formed from any suitable material that selectively and controllably changes length. In embodiments where a thermally activated length changing material is used, the operating temperature of such material can be less than or equal to approximately 40 degrees Celsius.

In the illustrated embodiment, the wound cover 24''' can comprise a flexible sheet member 66 that can be secured to a healthy skin 58 surrounding the wound site 22 with adhesive 60. In the illustrated embodiment, the flexible sheet member 66 is circular in shape. However, the shape of the flexible sheet member 66 is not so limited. The flexible sheet member 66 can define any shape disclosed above, or can be any other shape suitable or desired for the intended application. Similarly, the flexible sheet member 66 can be formed from any material disclosed above, or from any material that is suitable or desired for the intended application.

In some embodiments, as in the illustrated embodiment, the wound cover 24''' can comprise a semi-rigid support member 70 that can be positioned approximately adjacent to the peripheral edge of the flexible sheet member 66 and a length changing member 72 that can be secured to the top surface of the flexible sheet member 66 with one or more straps 74. In the illustrated embodiment, the support member 70 can generally define an annular shape and can be adhered to, laminated to, or otherwise attached to the top surface of the flexible sheet member 66 using any suitable method or material. In some embodiments, the support member 70 can be impregnated within or formed integrally with the flexible sheet member 66. In the illustrated embodiment, the support member 70 can have two pairs of opposing support tabs 76 configured to receive and support the end portions 72*a* of the length changing member 72. The semi-rigid support member 70 and the support tabs 76 can be formed from a suitable rigid material and configured so as to retain their shape and/or rigidity when the length of the length changing member 72 increases. In this configuration, because the end portions 72*a* of the length changing member 72 can be held in a fixed position by the support tabs 76, when the length changing member 72 is increased (e.g., as a result of being subjected to an electric current or thermal energy), the length of the length changing member 72 can increase, which can cause the length changing member 72 to bend convexly. Thus, the support member 70, the length changing member 72, and the support tabs 76 can be configured so that the length changing member 72 will not deflect or bend concavely (i.e., toward the wound site 22) when the wound cover 24''' is subjected to a negative pressure.

In the illustrated embodiment, the length changing member 72 can comprise two linear portions that are integrally formed or joined in the middle so as to define a criss-cross pattern across the top of the flexible sheet member 66. In some embodiments, the length changing member 72 can comprise less than or more than two linear portions projecting radially from a center point of the wound cover 24'''. In some embodiments, the length changing member 72 can define any shape or configuration that is suitable for the desired application. In the illustrated embodiment, the length changing member 72 can be formed from a piezoelectric material such that, when an electrical current is supplied to the positive electrodes 78*a* whereby an electrical current flows from the positive electrodes 78*a* through the length changing member 72 and out through the negative electrodes 78*b*, the length changing member 72 can increase in length as described above. This can cause the wound cover 24''' to change from the generally collapsed position (illustrated in FIG. 10A) to the generally raised position (illustrated in FIG. 10B).

In some embodiments, the length changing member 72 can be biased so that, when the length changing member 72 bends, the length changing member 72 deflects in a direction away from the flexible sheet member 66 and the wound site 22 even when a negative pressure is supplied to the volume of space 68 between the flexible sheet member 66 and the wound site 22 (as illustrated in FIG. 10B). In some embodiments, as in the illustrated embodiment, the length changing member 72 can be formed in a bent shape so as to define a bend in a direction away from the flexible sheet member 66 when the length changing member 72 is in a relaxed state (e.g., before an electrical current has been applied thereto). In particular, with reference to FIG. 10A, the length changing member 72 can be formed so that, when the length changing member 72 is in the relaxed state, the length changing member 72 is bowed so that the middle portion 72b of the length changing member 72 is above the end portions 72a of the length changing member 72 when the length changing member 72 is in the orientation depicted in FIG. 10A. In this configuration, the pre-bent shape of the length changing member 72 can bias the length changing member 72 to bend in a direction away from the flexible sheet member 66 and the wound site 22 as opposed to bending toward the flexible sheet member 66 and the wound site 22 when the length of the length changing member 72 increases.

In the illustrated embodiment, the straps 74 can be sized and configured to secure the length changing member 72 to the flexible sheet member 66. The straps 74 can be formed from the same or different material as is used to form the flexible sheet member 66, and can be formed integrally with the flexible sheet member 66 or formed separately and adhered, fused, or otherwise attached to the flexible sheet member 66. In some embodiments, with reference to FIG. 10A, the straps 74 can be sized and configured to allow the flexible sheet member 66 to conform to the shape of the wound site 22 so that, when the wound cover 24''' is in the collapsed position (as illustrated in FIG. 10A), the flexible sheet member 66 can conform to the shape of the wound site 22 or wound packing material, if any, positioned between the flexible sheet member 66 and the wound site 22 even though the length changing member 72 is bowed away from the wound site 22. Further, in some embodiments, with reference to FIG. 10B, the straps 74 can be sized and configured to position the flexible sheet member 66 above the wound site 22 when the wound cover 24''' is in the raised position (as illustrated in FIG. 10B) so as to increase the volume of space 68 between the flexible sheet member 66 and the wound site 22 as compared to when the wound cover 24''' is in the collapsed position. In some embodiments, the size and number of straps 74 can be selected according to the size and shape of the flexible sheet member 66 or the length changing member 72, or according to the size and shape of the wound site 22. In some embodiments, the length changing member 72 can be adhered, laminated, or attached directly to the flexible sheet member 66 such that the straps 74 are not required.

In some embodiments, the control device 32 can be configured to provide an electrical current to the length changing member 72 through electrically conductive wires 80 that are connected to the positive electrodes 78a. Further, electrically conductive wires 82 can be connected to the negative electrodes 78b to complete the electrical circuit. In some embodiments, the amount of bending in the length changing member 72 and, hence, the position of the wound cover 24''' relative to the wound site 22, can be controlled in part by the magnitude of the electrical current supplied to the length changing member 72 by the control device 32. Therefore, in some embodiments, the control device 32 can be used to control the position of the wound cover 24''' so that the wound cover 24''' can be positioned in any of a wide range of positions between a generally collapsed position and a generally raised position. In some embodiments, the control device 32 can be configured to allow a user or medical practitioner to select the magnitude of the electrical current or otherwise control the position of the wound cover 24'''. In some embodiments, the control device 32 can be configured to change the position of the wound cover 24''' according to a predetermined program or in response to input from a user or a sensor or other component, as described below.

Additionally, in some embodiments, any of the dressings, wound covers, or apparatuses disclosed herein can be configured so that the level of pressure in the space between the wound cover and the wound can be regulated and controlled. For example, in some embodiments, the level of pressure in the space between the wound cover and the wound can be controlled so that the level of reduced pressure in the space does not substantially change when the wound cover is changed or moved between the generally raised position to the generally collapsed position (i.e., from the generally raised position to the generally collapsed position or any positions therebetween, or from the generally collapsed position to the generally raised position or any positions therebetween).

In some embodiments, the materials, size, and geometric configuration of the wound cover 24 (or any wound cover disclosed herein) can be chosen so that wound cover can remain flexible and compliant, and sufficiently adhered to the body, so that the wound cover can flex with the movement of the portion of the body surrounding the wound and remain affixed to the patient's body even when the wound cover changes from the raised position to the collapsed position or is inadvertently bumped, pulled, compressed, or otherwise impacted. Furthermore, in some embodiments, the wound cover 24, which in some embodiments can include the flexible sheet member 66, channels 50, and/or peripheral channel 51, can be formed from a material that is sufficiently transparent to allow a medical practitioner or patient to visually inspect the wound site or wound packing material without removing the wound cover 24 or a portion of the wound cover 24 from the body. In some embodiments, the visual inspection of the wound site 22 or wound packing material can assist the medical practitioner patient in determining when to change the configuration of the wound cover 24 from the raised configuration to the flexible configuration, or vice versa. Furthermore, any of the wound covers disclosed herein can have any suitable shape or size in addition to those disclosed herein including, but not limited to, rectangular, square, circular, ovular, triangular, trapezoidal, or any other desired or suitable shape.

The negative pressure wound therapy apparatus 20 can be configured so that the wound cover 24 can be changed from the raised configuration (e.g., the configuration shown in FIGS. 3a, 4a, and 5) to the collapsed configuration (e.g., the configuration shown in FIGS. 3b and 4b) in a number of different ways. In some embodiments, the wound cover 24 can be changed from the semi-rigid configuration to the collapsed configuration as a result of manual input from a user or medical practitioner through a switch, button, lever, or other suitable switching mechanism. Similarly, in some embodiments, the apparatus 20 can be configured such that a medical practitioner or other user can adjust the amount of positive pressure or suction that can be applied by the pressure pump 52 to the channels 50 of the wound cover 24. For example, in some embodiments, the pressure pump 52 and the vacuum system 26 can be supported within an enclosure having either a digital or analog set of controls configured to allow the user to vary the positive pressure supplied to the wound cover 24 or the amount of negative pressure supplied from the vacuum pump 30 to the wound site 22. In some embodiments, the pressure pump 52 and the vacuum system 26 can be controlled by the control device 32 to follow a predetermined program or cycle, wherein any or all of the values such as duration, magnitude of the positive pressure supplied to the channels 50, and the negative pressure supplied to the wound site 22, are generally preset or predetermined, or are adjustable by the practitioner or user.

As mentioned, in some embodiments, the components of the apparatus 20, including but not limited to the switch mechanism discussed above and the control device 32, can be configured to cycle the wound cover 24 between the semi-rigid configuration and the collapsed configuration according to a predetermined duration or frequency or according to a duration or frequency as set by the practitioner or user. For example, in some embodiments, the wound cover 24 can be changed from the semi-rigid configuration to the collapsed configuration approximately every five minutes. In some embodiments, the wound cover 24 can be changed as follows (though not so limited): alternating from the semi-rigid configuration to the collapsed configuration or vice versa approximately every 1 minute or less; or approximately every 1 to 5 minutes, or approximately every 5 to 10 minutes, or approximately every 10 to 20 minutes, or approximately every 20 to 40 minutes, or approximately every 40 to 60 minutes, or approximately every 1 to 4 hours, or approximately every 4 to 8 hours, or approximately every 8 to 24 hours or longer, or to or from the any value within these ranges. In addition to the configurations disclosed herein where a user can control the switch mechanism or other settings of the apparatus 20, in some embodiments, the apparatus 20 can be configured to comprise patient lock-out features, i.e. features that prevent a patient or person other than the medical practitioner administering the negative pressure wound therapy from adjusting or otherwise manipulating the switch mechanisms or other controls of the apparatus 20.

In some embodiments, the apparatus 20 can be configured to alternate the wound cover 24 at a non-uniform frequency between the rigid and the flexible configurations. For example, in some embodiments, the apparatus can be configured so that the wound cover 24 is in the semi-rigid configuration approximately 10% or less of the time, or between approximately 10% and approximately 20%, or between approximately 20% and approximately 30%, or between approximately 30% and approximately 40%, or between approximately 40% and approximately 50%, or between approximately 50% and approximately 60%, or between approximately 60% and approximately 70%, or between approximately 70% and approximately 80%, or between approximately 80% an approximately 90%, or between approximately 90% and approximately 100% of the time, while in the collapsed configuration the remainder of the time. As an example of the above listed ranges, a wound cover 24 with channels 50 inflated so that the wound cover 24 is in the semi-rigid configuration approximately 20% of the time means that, for every 1 minute that the wound cover 24 is in the semi-rigid configuration, the wound cover 24 will be in the collapsed configuration for approximately 4 minutes.

Although the apparatus 20 is not limited to the specific negative pressure ranges disclosed herein, the following are some of the typical negative pressure ranges that can beneficially promote wound healing or provide other benefits related to negative pressure wound therapy. For example, in some embodiments, the apparatus 20 can be configured so that the apparatus 20 can provide, and so that the wound cover 24 can accommodate, up to approximately 200 mmHg of negative pressure below the atmospheric level. It is to be understood that the values of negative pressure disclosed herein are relative to ambient pressure such that, for example, 200 mmHg of negative pressure would be approximately 560 mmHg in practical terms (where the ambient pressure is approximately 760 mmHg). In some embodiments, the wound cover 24 and other components of the apparatus 20 can be configured to provide greater than approximately 200 mmHg of negative pressure to the wound site, although this level of negative pressure may exceed the generally desired range for most wound therapy programs. For some embodiments of the apparatus 20, it may be desired to provide in excess of approximately 200 mmHg of negative pressure to a dressing for purposes of examining the wound cover, conduit, pump system, or other components of the apparatus 20 for leaks or other performance-based deficiencies or characteristics.

In some embodiments, the apparatus 20 including the wound cover 24 can be configured to provide as little as approximately 40 mmHg to approximately 80 mmHg of negative pressure to the wound. This level of negative pressure, i.e., approximately 40 mmHg to approximately 80 mmHg, is typically associated with greater patient comfort and compliance. Additionally, some embodiments of the apparatus 20 and wound cover 24 can be configured to provide and sustain less than approximately 40 mmHg at the wound site, although many wounds that are treated with the apparatus 20 would benefit from a greater level of reduced pressure. Some embodiments of the apparatus 20 can be configured to provide negative pressure levels in excess of approximately 80 mmHg, such as levels up to approximately 150 mmHg. Further, as discussed above, some embodiments of the apparatus 20 and wound cover 24 can be configured to provide a positive pressure (i.e., pressure in excess of atmospheric pressure) to the wound.

As discussed above, it may be particularly beneficial to provide a positive pressure to the wound cover 24 and, hence, the wound, to facilitate changing the wound cover 24 from the flexible type configuration or position to the semi-rigid configuration or position. In particular, some embodiments of the apparatus 20 can be configured to provide up to approximately 200 mmHg or more of positive pressure (i.e., approximately 200 mmHg above atmospheric pressure). Thus, some embodiments of the apparatus 20 and wound cover 24 can be configured to provide between approximately 200 mmHg or more above atmospheric pressure to approximately 200 mmHg or more below atmospheric pressure. However, because providing positive pressure to the space between the wound cover 24 and the wound may affect the seal between the wound cover 24 and the patient's healthy skin, the application of positive pressure to the wound cover 24 must be monitored closely and used carefully so that the seal between the wound cover 24 and the skin is maintained. For example, in some embodiments, the apparatus 20 can be configured so that changing the wound cover 24 from the flexible to the semi-rigid configuration maintains approximately 100% to 50% of the level of negative pressure provided by the vacuum system 26 to the wound site.

Also, some embodiments of the apparatus 20 can be configured to permit a medical practitioner or user to set a maximum positive or negative pressure level that the vacuum system 26 of the apparatus 20 cannot exceed. Additionally, particular pressure ranges may be more suitable for either the semi-rigid configuration or the flexible configuration. For example, for a particular patient and for a particular wound, beneficial operating pressures may depend on whether the wound cover 24 is in the semi-rigid configuration or the collapsed configuration. To accommodate this, some embodiments of the apparatus 20 can be configured so that the negative pressure levels provided by the apparatus 20 to the wound are dependent on the position or configuration of the wound cover 24. As one non-limiting example, some embodiments of the apparatus 20 can be configured such that the negative pressure level provided to the wound cover 24 in the semi-rigid configuration is between approximately 60 mmHg-approximately 80 mmHg, while the negative pressure level provided to the wound cover 24 in the collapsed configuration is between approximately 40 mmHg-approximately 60 mmHg. Additionally, some embodiments of the apparatus 20 can be configured such that a medical practitioner or user has the ability to adjust the level of the negative pressure applied to the wound based on the configuration of the wound cover 24.

In some embodiments, as will be described in greater detail below, the apparatus 20 can further comprise monitors or sensors such as, but not limited to, temperature sensors, pressure sensors, blood flow sensors, blood oxygen saturation sensors, red blood cell perfusion sensors, or transcutaneous oxygen tension sensors positioned within the wound bed or adjacent to the wound bed. In some embodiments, sensors for surface application (for example, for application to the dermis or wound bed) can be used. In some embodiments, sensors that are implantable in the body or otherwise invasively applied, can be used. In particular, in some embodiments, the sensors can be positioned inside of the wound cover so as to be positioned between the wound cover and the wound. In some embodiments, the sensors can be positioned at least partially within the wound cover or, in some embodiments, positioned outside of the wound cover 24 preferably on the surface of or implanted within the healthy skin adjacent to the wound 22.

As mentioned, in some embodiments, the sensor or sensors can include, but are not limited to, sensors that can detect the temperature of the wound and/or blood flowing into the wound, the pressure within the wound cover, the rate of blood flowing into or adjacent to the wound, or the gas content of blood flowing into or adjacent to the wound, such gases including but not limited to oxygen, carbon dioxide, or other blood gases typically present in the body. Additionally, transcutaneous oximetry apparatuses and sensors used to detect transcutaneous oxygen tension in or adjacent to the wound bed can incorporated into any of the suitable embodiments of the apparatus 20 or used with any of the suitable wound covers 24 disclosed herein.

Any sensor presently known in the art that can be used to measure the parameters disclosed herein or other parameters of interest can be used with any of the embodiments of the apparatus 20 or wound cover 24 disclosed herein. Such sensors can include, but are not limited to, the apparatus for blood gas monitoring disclosed in U.S. Pat. No. 6,856,821 (titled "SYSTEM FOR COMBINED TRANSCUTANEOUS BLOOD GAS MONITORING AND VACUUM ASSISTED WOUND CLOSURE"), issued on Feb. 15, 2005 and incorporated by reference as if fully set forth herein. Additionally, without limitation, the pulsed light and blood oxygen content sensor system set forth in U.S. Pat. No. 5,040,538 (titled "PULSED LIGHT BLOOD OXYGEN CONTENT SENSOR SYSTEM AND METHOD OF USING SAME"), issued on Aug. 20, 1991 and incorporated by reference as if fully set forth herein, can also be used with the embodiments of the negative pressure wound therapy apparatus 20 described herein to determine the blood oxygen content within or adjacent to a wound site. Additionally, the transcutaneous oxygen monitor or monitors described in "Wound Healing Perspectives—A Clinical Pathway To Success" (http://www.nationalhealing.com/downloads/nhcwhpspring04.pdf), Volume 1, No. 4, Spring 2004, published by the National Healing Corporation which is incorporated by reference as if fully set forth herein, can be used with, or easily adapted for use with, any of the embodiments of the apparatus 20 or wound cover 24 disclosed herein.

Additionally, any sensor presently known in the art or later developed that can be used to measure the flow of blood or the perfusion of red blood cells into or adjacent to the wound site can be used with any of the embodiments of the apparatus 20 or wound cover 24 disclosed herein. Such sensors can include, but are not limited to, the OxyFlo2000, the OxyFlo4000, OxyLab LDF laser Doppler tissue blood perfusion monitors, or laser Doppler blood flow probes developed by Discovery Technology International, LLLP (http://www.discovtech.com/PAGE1.htm), any of which may be suitable for use with any of the embodiments of the apparatus 20 or wound cover 24 disclosed herein. In some embodiments, ultrasonic blood flow measurement devices which, in some cases, are based on the laser Doppler technology, can be adaptable for use with the present embodiments to be used to measure of the flow of blood into the tissue in the wound bed or adjacent to the wound site.

Capillary laser Doppler devices that are implanted within the wound site or adjacent to the wound site may provide the most accurate readings of blood flow or the perfusion of red blood cells into or adjacent to the wound site. Further, in some embodiments, transfused blood oxygen sensors that are currently available in the art or that are later developed can be configured for use with the apparatus 20. In some embodiments, the transfused blood oxygen sensors may need to be calibrated or adjusted for the operating pressure at the wound site to yield accurate data. The calibration for the operating pressure at the wound site could be programmed into the control device or other device that controls the sensors and/or collects the data gathered by the sensors. In some embodiments, it may be possible to measure transfused carbon dioxide levels using such sensors.

Because the semi-rigid configuration can increase the amount of blood flow to the wound site 22 at a particular negative pressure value as compared to the collapsed configuration, merely changing the wound cover 24 from the flexible configuration to the semi-rigid configuration can result in a blood flow increase to the wound site 22. Lack of sufficient blood flow to the wound site 22 is one reason why chronic wounds do not heal optimally. Conversely, in some embodiments, the collapsed configuration can exert a physical contact pressure on the tissue at the wound sites 22 so as to partially close the capillaries, arteries, or other blood vessels so that the blood flow rate to the wound site decreases. This may be advantageous when the wound is aspirating at a higher than desired rate.

In some embodiments, the sensors can be used to automatically trigger the control device 32 to change the wound cover 24 from the semi-rigid configuration to the collapsed configuration once the readings from the sensors reaches a particular or predetermined value (i.e., a threshold or trigger value), such as but not limited to preprogrammed values or changes in values related to blood flow or blood oxygen saturation levels. For example, in some embodiments, the threshold value that can trigger the change in the configuration of the wound cover 24 can be based on changes in the sensor readings (such as, but not limited to, changes in blood flow rate or blood oxygen saturation level) as compared to optimal or average values in the patient's body at or near the wound site or at another suitable bodily location. As such, in some embodiments, the trigger or predetermined value can be based on changes determined at the wound site from the sensors or can be based on the difference between the values determined at the wound site compared to values determined by suitable sensors at another bodily location. The trigger or predetermined value or values can be based on changes determined at the wound site or at another bodily location relative to readings taken prior to or during the negative pressure wound therapy at the wound site or at another bodily location.

Accordingly, in some embodiments, when the measurements (such as blood flow rate or rate of aspiration of exudate) acquired by the sensor or sensors exceed an optimal or predetermined value, the apparatus 20 can be configured so that the wound cover 24 is changed to the, or remains in the, collapsed configuration until the blood flow rate to the wound site 22 falls to a predetermined or suitable level. For example, in some embodiments, when the blood flow rate or the rate of aspiration of exudate from the wound determined by the appropriate sensor exceeds approximately 120% of the patient's optimal or average blood flow rate or aspiration rate, the apparatus 20 can be configured so that the wound cover 24 is automatically changed to the, or remains in the, collapsed configuration until the blood flow rate or aspiration rate falls below a particular value—which can be 120% of the patient's optimal or average rate, or another predetermined relative value. In some embodiments, the apparatus 20 can be configured so that the wound cover 24 is automatically changed to the, or remains in the, collapsed configuration when the value determined by the sensor exceeds approximately 110% or less, or from approximately 110% to approximately 120%, or from approximately 120% to approximately 130% or more of the patient's optimal value or average bodily value. The patient's optimal value may be determined as the optimal value at the wound site, or may be an optimal value based on sensor readings at other bodily locations. Additionally, the control device 32 can be configured to control the level of negative pressure between the wound cover 24 and the wound 22 depending on the value determined by the sensor or sensors. Further, as discussed in greater detail below, the apparatus 20 can be configured such that an alarm is triggered when such threshold values are reached.

Similarly, in some embodiments, when the measurements (such as blood oxygen saturation, temperature, or red blood cell perfusion rate) acquired by the sensor or sensors drop below an optimal or predetermined value, the apparatus 20 can be configured so that the wound cover 24 is changed to the, or remains in the, raised configuration until the respective value increases to a predetermined or suitable level. For example, in some embodiments, when the blood oxygen saturation, temperature, or red blood cell perfusion rate determined by the appropriate sensor drops below approximately 80% of the patient's optimal or average value, the apparatus 20 can be configured so that the wound cover 24 is automatically changed to the, or remains in the, raised configuration until the readings for the respective value increases to or above a particular value—which can be 80% of the patient's optimal or average value, or another predetermined relative value. In some embodiments, the apparatus 20 can be configured so that the wound cover 24 is automatically changed to the, or remains in the, raised configuration when the value determined by the sensor drops below approximately 90% or greater, or from approximately 90% to approximately 80%, or from approximately 80% to approximately 70%, or from approximately 70% to approximately 50% or less of the patient's optimal value or average bodily value. The patient's optimal value may be determined as the optimal value at the wound site, or may be an optimal value based on sensor readings at other bodily locations.

As mentioned, in some embodiments, the threshold or trigger values disclosed herein can be based on changes in such values determined by the sensors at the wound site or the difference between the value or values determined by the sensors at the wound site as compared to other bodily locations. The control device 32 can be configured to calculate such differences and determine when the threshold or trigger value has been reached. In some embodiments, however, the threshold or trigger values can be a straight forward value preprogrammed into the control device 32, or can be input by the user or practitioner of the apparatus 20.

Figure 11:
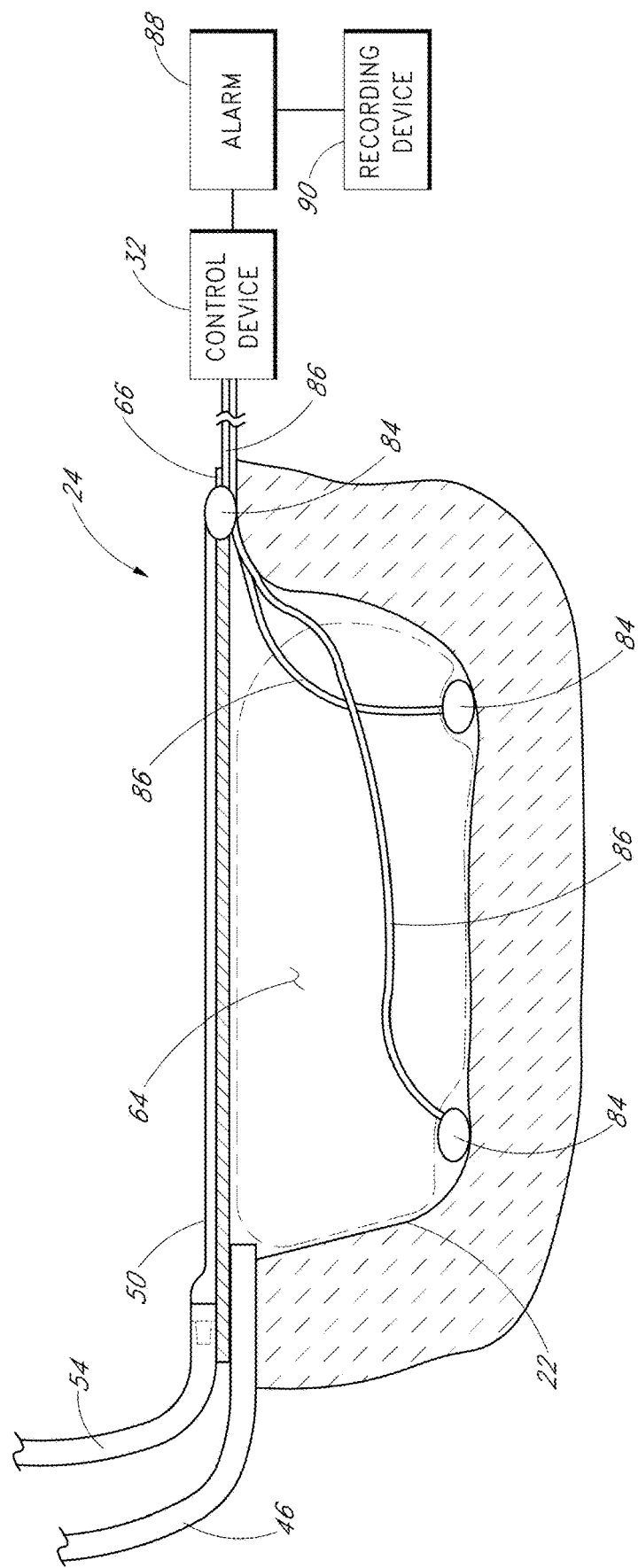
FIG. 11 is a schematic representation a portion of another embodiment of a negative pressure wound therapy apparatus, illustrating the wound cover in the deflated configuration.

FIG. 11 is a schematic representation of a portion of the apparatus 20 in which a pair of sensors 84 can be positioned in the wound bed 22. Note that, in FIG. 11, the wound cover 24 is shown in the deflated or collapsed configuration. By inflating the channels 50, the wound cover 24 could be changed from the collapsed configuration to the semi-rigid configuration. The wound cover 24 can be secured to the healthy skin surrounding the wound with adhesive (not shown) or by any other suitable method. Either of the sensors illustrated in FIG. 11 can be a temperature, pressure, blood flow, or blood oxygen saturation level sensor, or other any other suitable sensor currently available or later developed. As illustrated in FIG. 11, the sensors 84 can be connected to the control device 32 via leads 86. The leads 86 can be cables or wires constructed of an electrically conductive material, optical fiber, or other suitable medium arranged to enable data transmission from the sensors 84 to the control device 32, alarm device 88, recording device 90, and/or a visual display (not shown). The leads 86 can be sealably routed under the wound cover 24 in a manner that is similar to that for the conduit 46 so as to maintain the gas and fluid impermeable or semi-impermeable nature of the seal of the wound cover 24 to the body.

In some embodiments, only one sensor 84 can be positioned in the wound bed 22, but the apparatus 20 is not so limited. In some embodiments, any number of sensors 84 can be positioned in the wound bed 22. With reference to FIG. 11, the apparatus 20 can comprise a control device 32, an alarm device 88, and/or other recording device 90. In some embodiments, however, the apparatus 20 can comprise only the control device 32. The control device 32 can receive signals from the sensors 84 and converts the signals to an electronic or other suitable form that can be recognized by the alarm device 88. Accordingly, neither the alarm device 88 nor the recording device 90 is required in some arrangements of the apparatus 20. The alarm device 88 and the recording device 90 are supplemental components that can be added to the apparatus 20 to warn the user or practitioner when the values determined by the sensors 84 exceed predetermined values associated with the sensors 84, and to record the values transmitted from the sensors 84 over a predetermined amount of time, respectively. As such, the apparatus 20 illustrated in FIG. 11 can operate without the addition of the alarm device 88 and/or recording device 90.

The alarm device 88 can produce any type of audible sound when activated, such as a ringing sound, buzzing, chirping or any other common alarm noise. Alternatively, the alarm device 88 can include a digitally produced audible voice that presents pre-arranged messages corresponding to different conditions in the area of the wound site 22. The alarm device 88 can produce different levels of the alarm depending upon the magnitude of the measurements received from the sensors 84. For example, if the blood flow rate or temperature drops below or rises above predetermined values, as measured by the sensors 84, the alarm device 88 can sound successive alarm pitches, sounds, messages or series of sounds. Similarly, as the blood oxygen saturation level measured by any of the one or more sensors 84 falls below or rises above a predetermined value, the apparatus 20 can be configured to alert the user. As mentioned above, the control device 32 can also control the vacuum pump 30 or the positive pressure pump 52 to either adjust the negative pressure under the wound cover 24, or positive pressure in the channels 50 in the wound cover 24, respectively, so that the negative pressure under the wound cover 24 or the configuration of the wound cover 24 can be adjusted in response to the data collected by the sensors 84.

The recording device 90 can be any device designed to record data received from the sensors 84. Such devices can be capable of recording data on compact disks, DVD disks, floppy disks, magnetic tape, integrated circuits, or other similar media in digital form. Alternatively, the recording device 90 can be a "manual" device that records or displays data through a chart recorder or visual electronic display, such as an LCD or CRT monitor. Such information can be in the form of real-time data, or an average over a predetermined duration of time, or any other suitable form. In some embodiments information regarding blood flow could be displayed as follows: (i) Blood Flow Steady; (ii) Blood Flow Increasing; or (iii) or Blood Flow Decreasing. In some embodiments, information regarding blood oxygen saturation level could be displayed as follows: (i) Oxygen Level Steady; (ii) Oxygen Level Increasing; or (iii) or Oxygen Level Decreasing. Thus, the apparatus 20 or display could embody this information that is being gathered by one or more of the sensors 84 to help with the wound healing as well as provide important information to a health care practitioner studying the effects of such parameters on wound healing.

FIG. 12 is a schematic representation of a portion of the apparatus 20 in which multiple sensors 84 are positioned on the inside surface of the member 66 of the wound cover 24. As is illustrated, the wound cover 24 is shown in the rigid or raised configuration. In some embodiments, the sensors 84 and/or leads 86 can be adhered to the inside surface of the member 66, or otherwise supported by the member 66. Alternatively, in some embodiments, the sensors 84 and/or leads 86 can be integrated into the member 66 during the manufacture of the wound cover 24. For example, the sensors 84 and leads 86 can be placed between one or more layers comprising the member 66 so as to be formed integral therewith. If necessary, the portion of the material comprising that member 66 that is adjacent to the sensors 84 can be removed prior to use so that the functionality of the sensors 84 will not be obstructed or attenuated by the material in the wound cover 24. The sensors 84 and leads 86 can be sized and configured so as to not irritate or otherwise damage any of the tissue in or around the wound bed 22 when the wound cover 24 is changed from the semi-rigid configuration (as shown in FIG. 12) to the collapsed configuration. In some configurations, the sensors 84 and leads 86 can be covered with a cotton gauze or other suitable material that will not affect the sensors ability to collect the desired information from the wound bed 22, but that will protect the wound bed 22 from any damage that may occur if the sensors 84 or the leads 86 contact the wound bed 22.

In some embodiments, not shown, one or more of the sensors 84 can be positioned within the absorbable matrix or other dressing material positioned within the wound bed. Alternatively, in some embodiments, one or more sensors 84 can be positioned on or in the fluid collection system 28 to change the configuration of the wound cover 24 from a rigid configuration to the flexible configuration when the rate at which exudate enters the fluid collection system 28 exceeds a predetermined value. As mentioned above, the blood flow through the wound site 22, and, accordingly, the exudate produced by the wound may be lower when the wound cover 24 is in the collapsed configuration than when the wound cover 24 is in the semi-rigid configuration. Additionally, the apparatus 20 can be configured such that the amount of negative pressure supplied to the wound site 22 is decreased when the amount of exudate in the fluid collection system 28, or the rate at which exudate flows into the fluid collection system 28, exceeds predetermined values.

While the above detailed description has shown, described, and pointed out novel features as applied to various embodiments, it will be understood that various omissions, substitutions, and changes in the form and details of the device or process illustrated can be made without departing from the spirit of the disclosure. Additionally, the various features and processes described above can be used independently of one another, or can be combined in various ways. All possible combinations and subcombinations are intended to fall within the scope of this disclosure.

As will be recognized, certain embodiments disclosed herein can be embodied within a form that does not provide all of the features and benefits set forth herein, as some features can be used or practiced separately from others. The scope of the inventions is indicated by the appended claims rather than by the foregoing description. All changes which come within the meaning and range of equivalency of the claims are to be embraced within their scope.

What is claimed is:

1. An apparatus for administering reduced pressure treatment to a wound on a body, the apparatus comprising:
   a wound cover configured to be placed over and enclose the wound so as to define a space between at least a portion of the wound cover and the wound and to maintain a reduced pressure in the space when reduced pressure is applied to the space, wherein the wound cover has a first configuration and a second configuration when placed over the wound;
   a vacuum pump configured to provide reduced pressure to a space between the wound cover and the wound;
   a sensor configured to detect a flow rate of blood adjacent to the wound, the detection occurring through the intact dermis adjacent to the wound; and
   a control device configured to control application of reduced pressure applied to the space between the wound cover and the wound and configured to selectively change the configuration of the wound cover based at least on a detection of a flow rate of blood adjacent to the wound.

2. The apparatus of claim 1, wherein the wound cover is configured to move between a raised configuration and a collapsed configuration.

3. The apparatus of claim 1, wherein the control device is configured to change the configuration of the wound cover when the flow rate of blood flowing into or adjacent to the wound is above or below a predetermined value.

4. The apparatus of claim 1, wherein the control device is configured to increase or decrease an amount of reduced pressure supplied to the wound when the flow rate of blood flowing into or adjacent to the wound is below or above a predetermined value, respectively.

5. The apparatus of claim 1, further comprising a sensor configured to detect an amount of oxygen in a portion of the blood flowing into or adjacent to the wound.

6. The apparatus of claim 5, wherein the control device is configured to change the configuration of the wound cover when an amount of oxygen in a portion of the blood flowing into or adjacent to the wound is above or below a predetermined value.

7. The apparatus of claim 5, wherein the control device is configured to increase or decrease an amount of reduced pressure supplied to the wound when the amount of oxygen in a portion of the blood flowing into or adjacent to the wound is below or above a predetermined value, respectively.

8. The apparatus of claim 1, wherein the sensor comprises a light emitting sensor.

9. The apparatus of claim 8, wherein the sensor comprises a laser Doppler sensor.

10. The apparatus of claim 1, wherein the first configuration comprises a rigid, upright configuration that resists collapse under negative pressure and the second configuration comprises a flexible configuration that collapses under negative pressure.

11. The apparatus of claim 1, wherein the control device is configured to change the configuration of the wound cover when the detected blood flow rate adjacent the wound crosses a threshold determined by a second sensor.

12. An apparatus for administering reduced pressure treatment to a wound on a body, the apparatus comprising:
  a wound cover for covering a wound and facilitating application of negative pressure wound therapy to the wound, the wound cover comprising:
    a flexible cover sized and configured to be placed over and enclose the wound so as to create a space between the cover and the wound; and
    a seal configured to seal at least a portion of the cover to a portion of tissue surrounding the wound such that a reduced pressure is maintained in the space between the cover and the wound when the cover is placed over the wound and the space is supplied with reduced pressure, wherein the cover is configured such that at least a portion of the cover can be selectively moved between at least a raised position and a collapsed position when the cover is placed over the wound and the space is supplied with reduced pressure;
  a vacuum pump configured to provide reduced pressure to the space between the cover and the wound;
  a control device configured to control a level of reduced pressure applied to the space between the wound cover and the wound and configured to selectively move at least a portion of the cover between at least the raised position and the collapsed position when the cover is placed over the wound and the space is supplied with reduced pressure, wherein the control device is configured to increase the amount of reduced pressure supplied to the wound when a flow rate of blood adjacent the wound falls below a predetermined value; and
  a sensor configured to detect a flow rate of blood adjacent to the wound, the detection occurring through the intact dermis adjacent to the wound.

13. The apparatus of claim 12, further comprising at least one sensor supported by the cover configured to provide data to the control device, the control device being configured to accept an input of the data and to process the data.

14. The apparatus of claim 12, wherein the control device is configured to move at least a portion of the cover to the raised position or maintain at least a portion of the cover in the raised position when the flow rate of blood flowing into or adjacent to the wound falls below a predetermined value.

15. The apparatus of claim 12, wherein the control device is configured to move at least a portion of the cover to the collapsed position or maintain at least a portion of the cover in the collapsed position when the flow rate of blood flowing into or adjacent to the wound rises above a predetermined value.

16. The apparatus of claim 12, further comprising a sensor configured to detect an amount of oxygen in a portion of the blood flowing into or adjacent to the wound.

17. The apparatus of claim 12, wherein the control device is configured to move at least a portion of the cover to the raised position or maintain at least a portion of the cover in the raised position when the amount of oxygen in a portion of the blood flowing into or adjacent to the wound falls below a predetermined value.

18. The apparatus of claim 12, wherein the control device is configured to increase the level of the reduced pressure supplied to the wound when the amount of oxygen in a portion of the blood flowing into or adjacent to the wound falls below a predetermined value.

19. The apparatus of claim 12, wherein the control device is configured to move at least a portion of the cover to the collapsed position or maintain at least a portion of the cover in the collapsed position when the amount of oxygen in a portion of the blood flowing into or adjacent to the wound rises above a predetermined value.

20. The apparatus of claim 12, wherein the control device is configured to decrease the level of the reduced pressure supplied to the wound when the amount of oxygen in a portion of the blood flowing into or adjacent to the wound rises above a predetermined value.

21. An apparatus for administering reduced pressure treatment to a wound on a body, the apparatus comprising:
  a wound cover for covering a wound and facilitating application of negative pressure wound therapy to the wound, the wound cover comprising:
    a flexible cover sized and configured to be placed over and enclose the wound so as to create a space between the cover and the wound; and
    a seal configured to seal at least a portion of the cover to a portion of tissue surrounding the wound such that a reduced pressure is maintained in the space between the cover and the wound when the cover is placed over the wound and the space is supplied with reduced pressure, wherein the cover is configured such that at least a portion of the cover can be selectively moved between at least a raised position and a collapsed position when the cover is placed over the wound and the space is supplied with reduced pressure;
  a vacuum pump configured to provide reduced pressure to the space between the cover and the wound;
  a control device configured to control a level of reduced pressure applied to the space between the wound cover and the wound and configured to selectively move at least a portion of the cover between at least the raised position and the collapsed position when the cover is placed over the wound and the space is supplied with reduced pressure, wherein the control device is configured to decrease the amount of reduced pressure supplied to the wound when a flow rate of blood adjacent the wound rises above a predetermined value; and a sensor configured to detect a flow rate of blood adjacent to the wound the detection occurring through the intact dermis adjacent to the wound.

* * * * *

UNITED STATES PATENT AND TRADEMARK OFFICE
CERTIFICATE OF CORRECTION

PATENT NO. : 11,058,807 B2
APPLICATION NO. : 15/441899
DATED : July 13, 2021
INVENTOR(S) : Richard Scott Weston Page 1 of 1

It is certified that error appears in the above-identified patent and that said Letters Patent is hereby corrected as shown below:

On the Title Page

On Page 3, Column 2, Item (56), Line 33, under Other Publications, delete "D.A." and insert --D.A.,--.

On Page 4, Column 2, Item (56), Line 5, under Other Publications, delete "Salmoncida:" and insert --Salmonicida:--.

In the Specification

In Column 6, Line 67, delete "duration" and insert --duration.--.

In Column 16, Line 8, delete "napthalate," and insert --naphthalate,--.

In Column 16, Line 44, delete "FIG." and insert --FIGS.--.

In Column 21, Line 12, delete "biase" and insert --bias--.

In the Claims

In Column 33, Claim 21, Line 2, delete "wound" and insert --wound,--.

Signed and Sealed this
Twenty-fourth Day of August, 2021

Drew Hirshfeld
*Performing the Functions and Duties of the*
*Under Secretary of Commerce for Intellectual Property and*
*Director of the United States Patent and Trademark Office*